United States Patent
Kuntz et al.

(10) Patent No.: US 8,377,065 B2
(45) Date of Patent: Feb. 19, 2013

(54) SURGICAL INSTRUMENT FOR FIXING A CLAMP TO A BONE FIXATION DEVICE

(75) Inventors: Kyle Kuntz, West Chester, PA (US); Josef Gabelberger, West Chester, PA (US); Zoher Bootwala, West Chester, PA (US); Edward McShane, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 322 days.

(21) Appl. No.: 12/789,073

(22) Filed: May 27, 2010

(65) Prior Publication Data

US 2010/0305625 A1 Dec. 2, 2010

Related U.S. Application Data

(60) Provisional application No. 61/181,558, filed on May 27, 2009.

(51) Int. Cl.
*A61B 17/88* (2006.01)

(52) U.S. Cl. .................................. 606/86 A; 606/246

(58) Field of Classification Search ............ 81/451–455; 606/86 A, 246, 278–279, 267, 277, 305–306, 606/324

See application file for complete search history.

(56) References Cited

U.S. PATENT DOCUMENTS

| | | | |
|---|---|---|---|
| 5,782,831 A | | 7/1998 | Sherman et al. |
| 5,910,141 A | * | 6/1999 | Morrison et al. ........... 606/86 A |
| 6,139,551 A | * | 10/2000 | Michelson et al. ............ 606/79 |
| 8,172,847 B2 | * | 5/2012 | Dziedzic et al. ............ 606/86 A |
| 2006/0025769 A1 | | 2/2006 | Dick et al. |
| 2009/0062859 A1 | * | 3/2009 | Mahoney et al. ............. 606/278 |
| 2009/0157125 A1 | * | 6/2009 | Hoffman et al. ............ 606/86 A |

FOREIGN PATENT DOCUMENTS

| | | |
|---|---|---|
| WO | WO2009/011929 A1 | 1/2009 |
| WO | WO 2009011929 A1 * | 1/2009 |
| WO | WO2010/138711 A2 | 12/2010 |

* cited by examiner

*Primary Examiner* — Kevin T Truong
*Assistant Examiner* — Larry E Waggle, Jr.
(74) *Attorney, Agent, or Firm* — Woodcock Washburn LLP

(57) ABSTRACT

A surgical instrument for moving a clamp relative to a bone anchor to properly position and secure the clamp to the bone anchor. The surgical instrument including a housing, a socket assembly, a manipulating assembly, a gripping assembly and a reduction assembly.

41 Claims, 19 Drawing Sheets

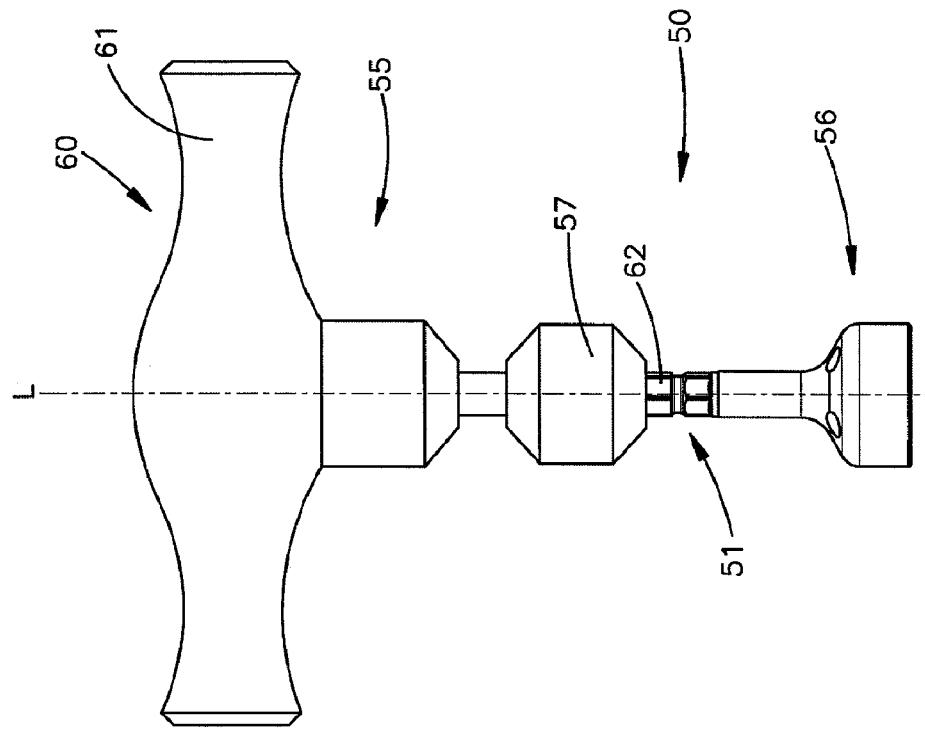
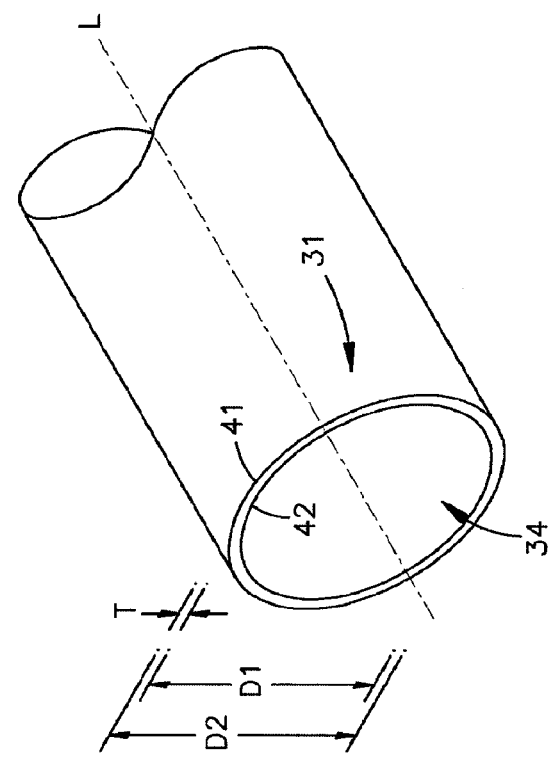

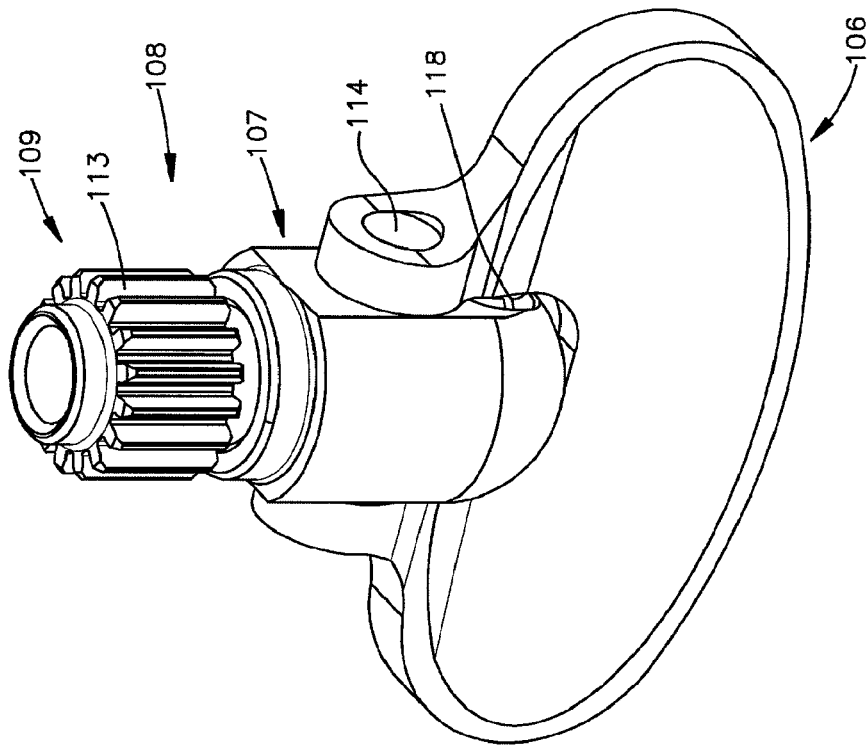
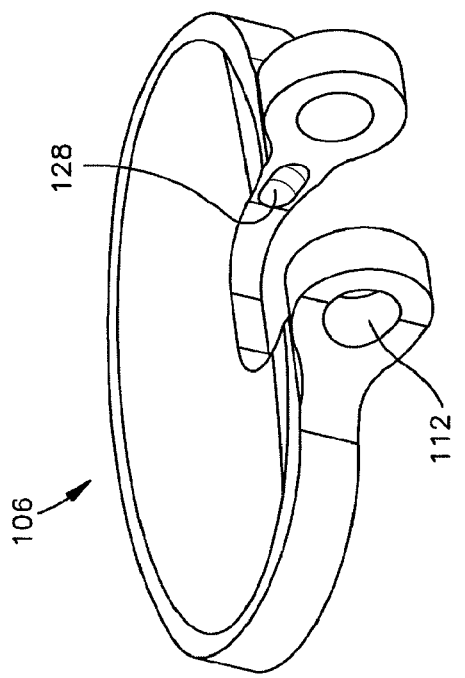
Fig.8C
Fig.8B

SURGICAL INSTRUMENT FOR FIXING A CLAMP TO A BONE FIXATION DEVICE

CROSS REFERENCE TO RELATED APPLICATIONS

This application claims priority to U.S. Provisional Application No.: 61/181,558, filed May 27, 2009, herein incorporated by reference in its entirety.

TECHNICAL FIELD

This disclosure relates generally to a surgical instrument used for fixing a clamp to a bone fixation device.

BACKGROUND

Spondylolisthesis is a condition in which a bone, typically a vertebra in the lower part of the spine, slips out of alignment with the bone below it. While adjacent vertebrae are normally aligned vertically, this slip results in the anterior portion of the superior vertebra to protrude in the anterior direction farther than the anterior portion of the inferior vertebra. If left untreated spondylolisthesis can cause pain in the lower back and legs. Spinal fusion surgery can be performed to treat the condition and relieve pain.

Spinal fusion is a procedure that involves joining two or more adjacent vertebrae with a bone fixation device to restrict movement of the vertebra with respect to one another. Spinal fixation devices are used in spine surgery to align, stabilize and/or fix a desired relationship between adjacent vertebral bodies. Such devices typically include a spinal rod, such as, for example, a relatively rigid fixation rod or a dynamic or flexible spinal rod, etc. (collectively referred to herein as a spinal rod), that is coupled to adjacent vertebrae by attaching the spinal rod to various bone fixation elements, such as, for example, hooks, bolts, wires, screws, etc. (collectively referred to herein as a bone anchor). Surgeons may commonly choose to install multiple bone anchors, as well as multiple spinal rods, to treat a given spinal disorder. In addition, surgeons may choose to incorporate one or more clamps to interconnect a spinal rod and bone anchor.

Traditionally, surgical techniques for spinal fusion have required the use of multiple instruments, each of which may require the use of more than one hand to operate. Thus, multiple surgeons may be required to manipulate the instruments required to perform a spinal fusion surgery. Also a number of bone anchor extension members of various shapes and sizes may be used to assist in the attachment of a clamp to the bone anchor. This results in a number of different instruments being required for each corresponding spinal fixation device or bone anchor extension member.

SUMMARY

A device or surgical instrument is provided that can move a clamp into a desired location with respect to a bone anchor, and secure the clamp to the bone anchor while requiring a reduced number of hands to operate and being adjustable to operate with a varying range of spinal fixation devices and extension members.

In accordance with one embodiment, an instrument is provided that moves a clamp relative to a bone anchor to properly position and secure the clamp to the bone anchor. More specifically, the device is used to grasp onto and/or pull on a cylindrical shaft such as, for example, a Schanz screw, an extension removably coupled to a bone anchor, etc. and to push on an implant such as, for example, a clamp used to secure a spinal rod to a bone anchor, to move the clamp relative to the bone anchor to locate the clamp in a predetermined location. The device may also include a mechanism configured to rotate the clamp tightening nut relative to the bone anchor to secure the clamp to the bone anchor.

BRIEF DESCRIPTION OF THE DRAWINGS

The foregoing summary, as well as the following detailed description of embodiments of the application, will be better understood when read in conjunction with the appended drawings. For the purposes of illustrating the present invention of the present application, there is shown in the drawings preferred embodiments. It should be understood, however, that the application is not limited to the precise arrangements and instrumentalities shown. In the drawings:

FIG. 4B is a perspective view of the socket assembly along line 4B-4B of FIG. 4A.

FIG. 5 is a side elevation view of the manipulating assembly illustrated in FIG. 2;

FIG. 8B is a perspective view of the gripping member illustrated in FIG. 8A.

FIG. 8C is a perspective view of the reduction assembly illustrated in FIG. 8 assembled together;

DETAILED DESCRIPTION OF ILLUSTRATIVE EMBODIMENTS

Figure 1B:
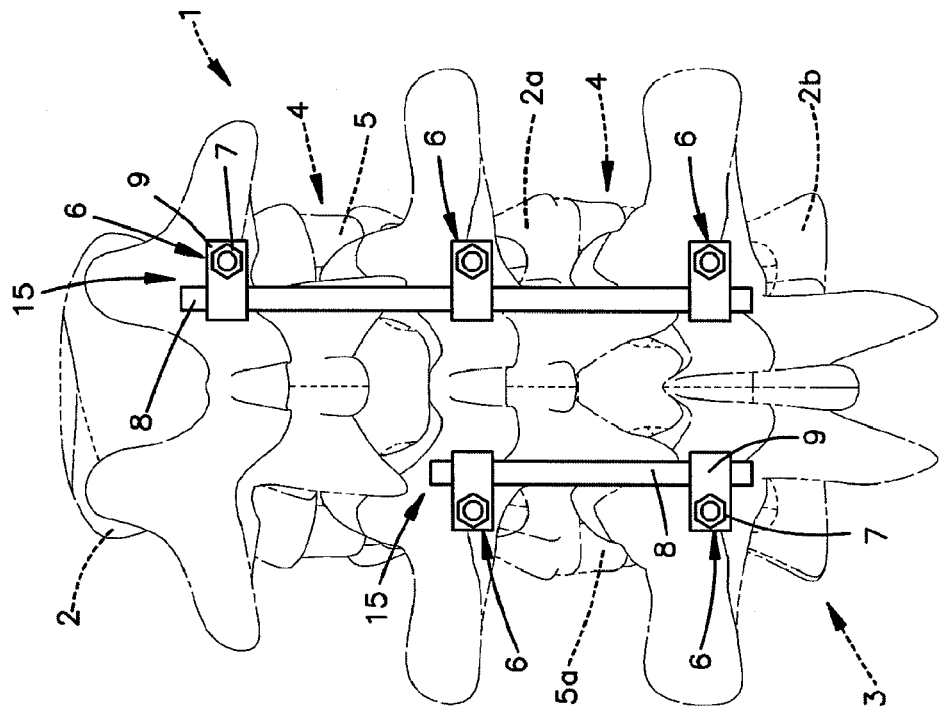
FIG. 1B is a rear elevation view of three adjacent vertebrae and two intervertebral spaces showing the placement of several bone fixation devices after a spinal fusion surgery has been performed.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the device and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to an insertion instrument for reducing (e.g., inserting and/or coupling) a clamp to a bone anchor in a spinal fixation procedure. The invention may have other applications and uses and should not be limited to the structure or use described and illustrated. While the surgical instrument will be described as and may generally be used in the spine (for example, in the lumbar, thoracic or cervical regions), those skilled in the art will appreciate that the surgical instrument may be used in connection with fixation of other parts of the body such as, for example, joints, long bones or bones in the hand, face, feet, extremities, cranium, etc.

Figure 1A:
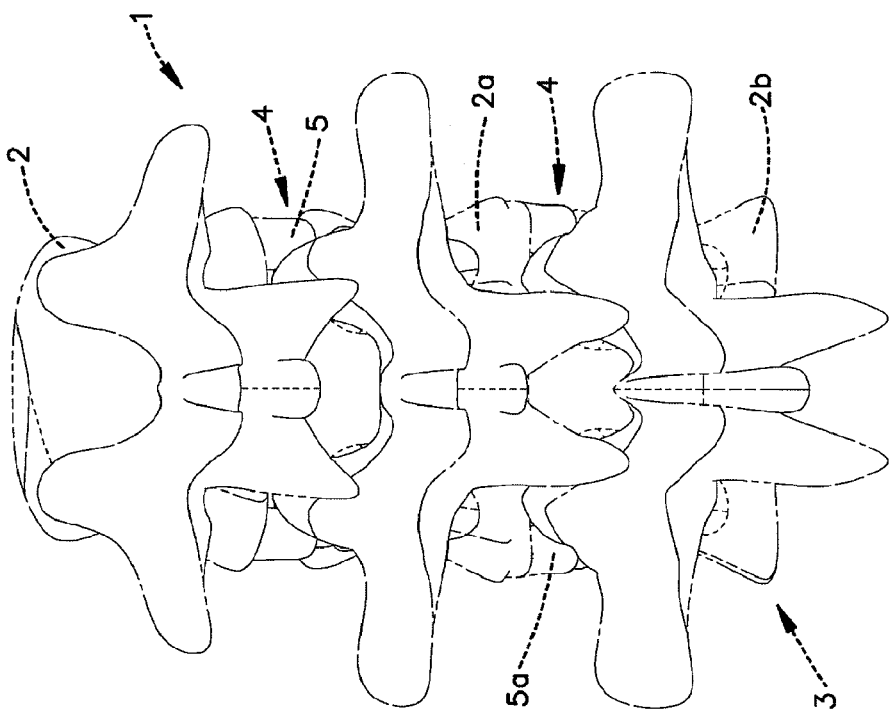
FIG. 1A is a rear elevation view of three adjacent vertebrae and two intervertebral spaces.

Referring to FIG. 1A, a spinal region 1 includes a number of adjacent vertebrae 2 arranged in a vertical column 3. Adjacent vertebrae 2 are separated by respective intervertebral disc spaces 4 that can retain a vertebral disc 5. Alternatively, the vertebral disc 5 may be removed, and a disc implant can be inserted into the intervertebral disc space 5. As illustrated, the spinal region 1 includes a superior vertebra 2a disposed above an inferior vertebra 2b and separated by a respective intervertebral disc space 5a.

Referring to FIG. 1B, a spinal fixation assembly 15 is configured to fuse adjacent vertebrae 2 together to correct a disease such as spondylolisthesis. The spinal fixation assembly 15 includes a plurality of spinal fixation devices 6, for instance at least a pair of spinal fixation devices 6, and a spinal fixation rod 8. Thus, the spinal fixation rod 8 spans across at least one intervertebral disc space 5. The bone anchors 7 are coupled to respective clamps 9, and implanted into respective vertebrae 2, for instance into the pedicles of the vertebrae 2. The spinal rod 8 extends through the respective clamps 9 so as to operatively couple the clamps 9 of the spinal fixation assembly 15, thereby operatively coupling the respective vertebrae 2. The bone anchor 7 may include a mechanism such as, for example, an internally threaded bore for receiving a threaded distal end of a bone anchor extension member 300 (see FIG. 3B). Alternatively, the bone anchor 7 may be a Schanz Screw, a post screw (e.g., a pre-cut Schanz Screw), etc. It should be understood that the spinal fixation assembly 15 is only one example of an assembly configured to operatively couple adjacent vertebrae, and that any suitable alternatively constructed spine fixation assembly could be implemented as desired.

Figure 2:
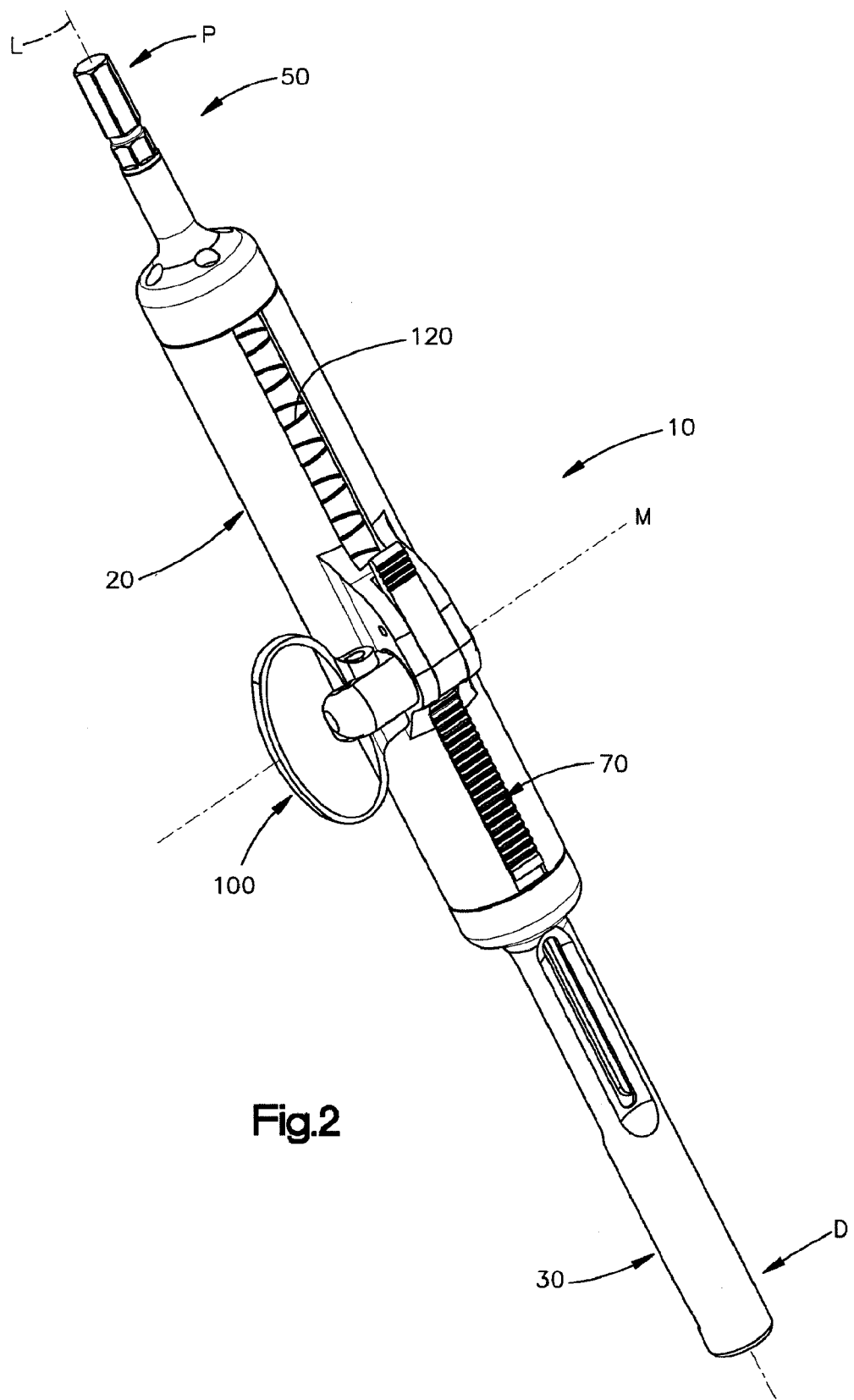
FIG. 2 is a perspective view of a surgical instrument constructed in accordance with one embodiment including a housing, a socket assembly, a manipulating assembly, a gripping assembly and a reduction assembly.
Figure 3A:
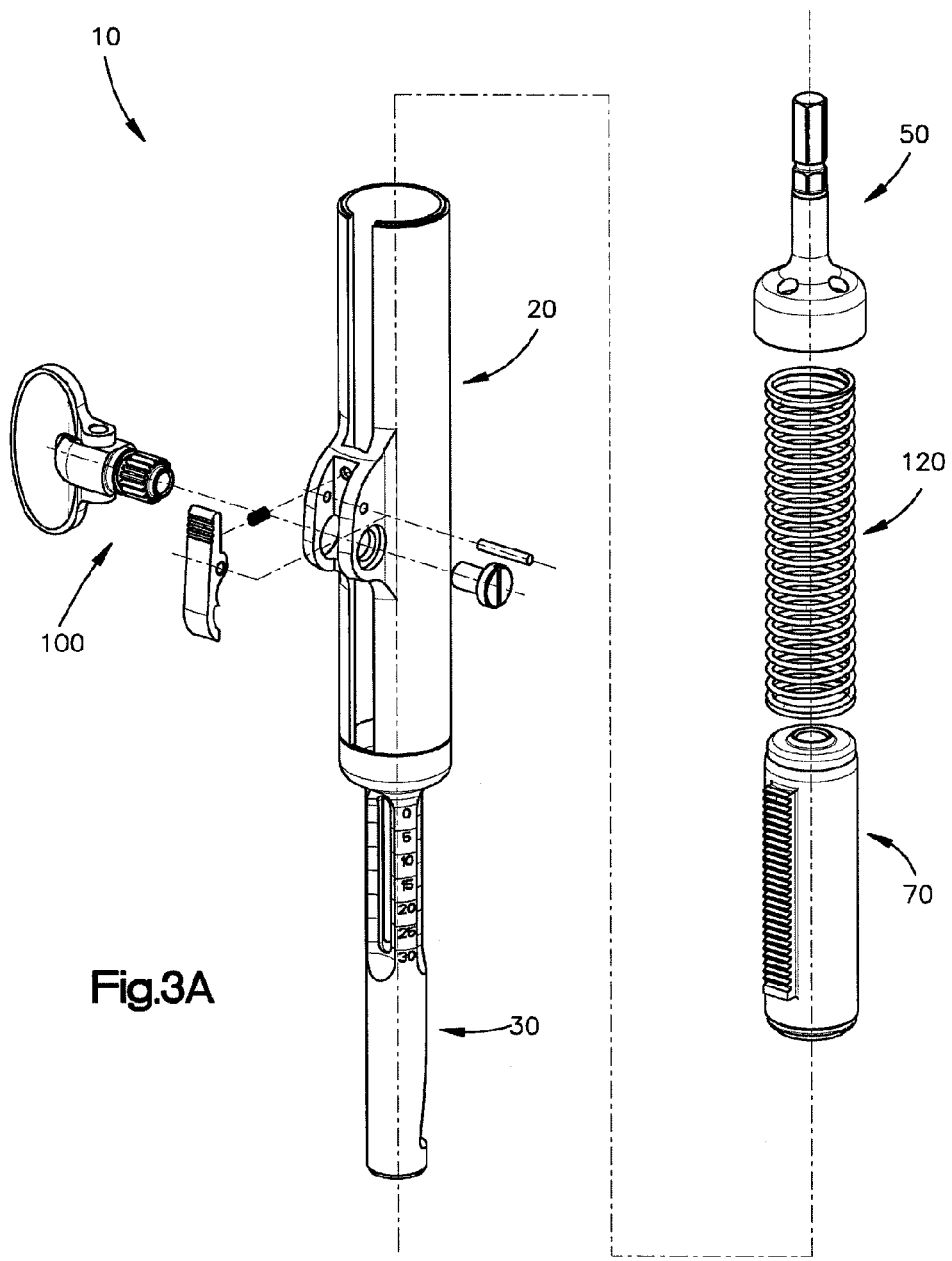
FIG. 3A is an exploded perspective view of the surgical instrument illustrated in FIG. 2.
Figure 3B:
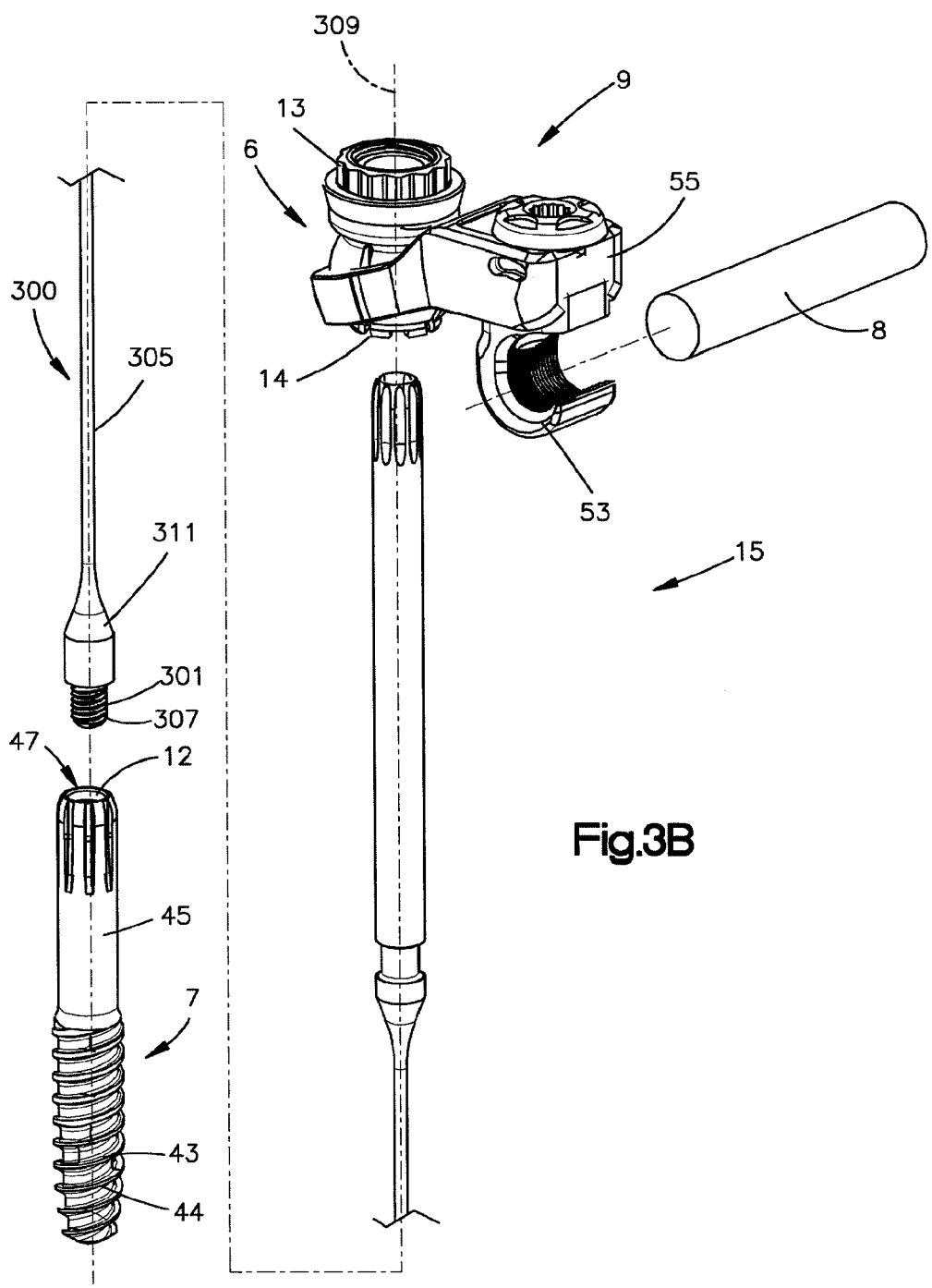
FIG. 3B is an exploded side elevation view of a spinal fixation device including a bone anchor, bone anchor extension member, spinal rod and clamp.
Figure 3C:
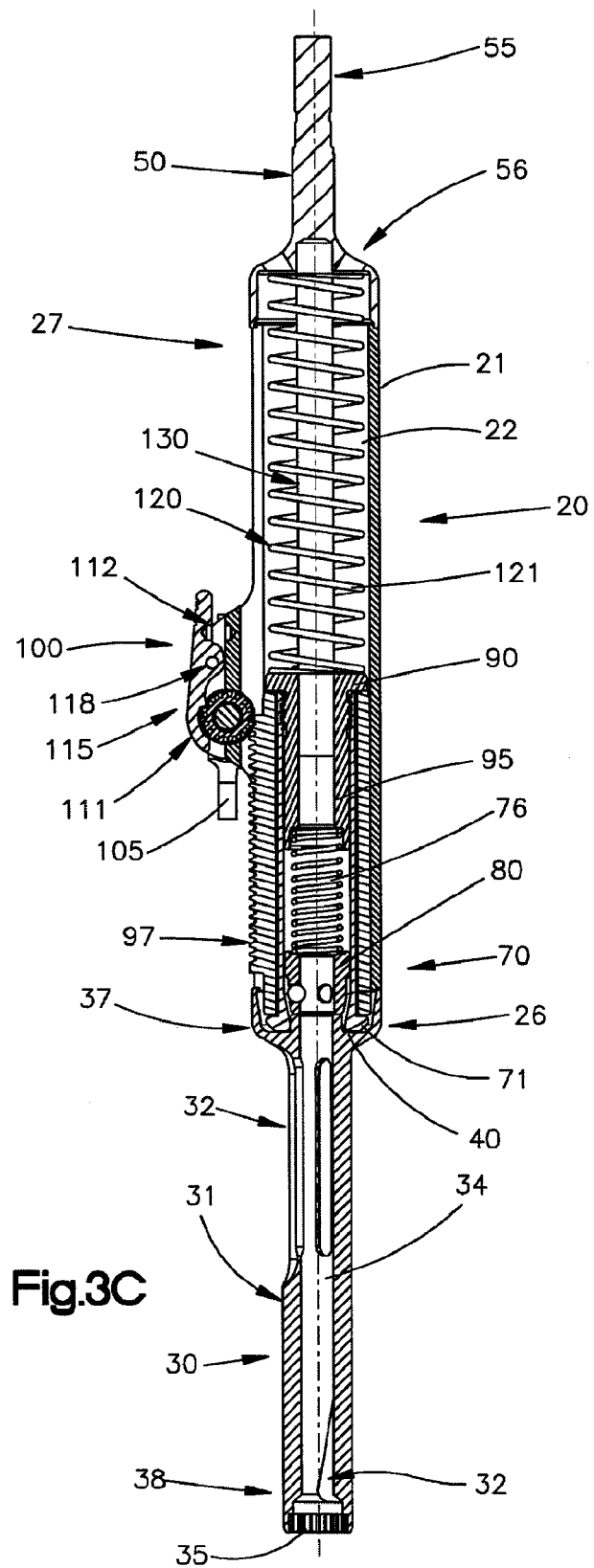
FIG. 3C is a cross-sectional view of the surgical instrument taken along line 3C-3C of FIG. 3A.

Referring to FIGS. 2-3C a surgical instrument 10 is configured to position and secure the clamp 9 to the bone anchor 7 that is implanted into a vertebra 2. The surgical instrument 10 extends centrally along a longitudinal axis L, and defines a proximal end P and a distal and D that is spaced from the proximal end P along the longitudinal axis L. A lateral direction M is also defined as illustrated which is perpendicular to longitudinal axis L. The surgical instrument 10 includes a housing 20, a socket assembly 30 having a proximal end 37 that is connected to the housing 20, and a manipulating assembly 50 having a distal end 56 that engages the housing 20. The surgical instrument further includes a gripping assembly 70 carried by the housing 20, a biasing member 120 disposed in the housing 20, and a reduction assembly 100 attached to the housing 20 and moveably coupled to the gripping assembly 70. The socket assembly 30 is configured to engage the clamp 9, and the gripping assembly 70 is configured to engage the bone anchor extension member 300. As described in more detail below, the reduction assembly 100 is configured to apply a force to the gripping assembly 70 which moves the socket assembly 30 toward the bone anchor 7 until the clamp 9 is in a desired position. When two or more clamps 9 are in their desired positions on bone anchors 7 and a spinal rod 8 is attached to the clamps 9, the spinal rod 8 operatively couples the adjacent vertebrae 2 in a proper vertical alignment.

Referring to FIG. 3B in particular, the spinal fixation assembly 15 includes the bone fixation device 6 and a spinal rod as described above. The bone fixation device 6 includes the bone anchor 7 and the clamp 9 as described above. During a spinal fusion surgery, the bone anchor 7 is secured to a vertebra 2. The bone fixation device 6 can further include a bone anchor extension member 300 that is configured to be secured to the bone anchor 7. In accordance with one embodiment, the extension member 300 includes an elongate body 303 that defines a proximal end 305 separated from a distal end 307 along a central axis 309. The extension member 300 further includes threads 301 that project out from the distal end 307 of the elongate body 303, and a stop member 311 that extends out from the body 303 at a location adjacent and proximate to the threads 301.

The bone anchor 7 includes a shaft 43 and a head 45 coupled to a proximal end of the shaft. The bone anchor 7 can be configured as a screw having threads 49 extending from the shaft 43 that are configured to be driven into a respective vertebra. Alternatively, the shaft 43 can be configured as a nail whose shaft is unthreaded or toothed or as a hook, so as to engage the underlying vertebra. The bone anchor 7 defines an aperture 47 extending into the head 45. The head 45 defines threads 12 disposed in the aperture 47. The threads 301 of the extension member 300 are configured to engage the corresponding threads 12 of the bone anchor 7 during operation. The threads 12 may be inner threads inside the bone anchor 7 as illustrated or outer threads to engage an extension member 300, or any other feature that can be selectively engaged and is able to transmit translational forces. Engagement between the stop member 311 and the head 45 of the bone anchor 7 limits the insertion of the distal end 307 of the extension member 300 into the aperture 47.

The clamp 9 includes a drive member 13, a spinal rod support member 53, and an arm 55 connected between the drive member and the spinal rod support member 53. The support member 53 is illustrated as a hook configured to carry the spinal rod 8, though it should be appreciated that the support member 53 can be configured as desired. In accordance with the illustrated embodiment, the drive member 13 is a 12-point nut, though it should be appreciated that the drive member 13 can be alternatively configured as desired. The clamp 9 also includes an inner bore 14 that extends through the drive member 13, and is sized to receive the bone anchor extension member body 303. The inner bore 14 is also sized to receive the anchor head 45. Once clamp 9 is in its desired position with respect to the bone anchor 7, the clamp 9 is secured to the bone anchor 7. Clamp 9 can be secured to bone anchor 7 using a collet-style or similar arrangement. A torque is applied to drive member 13 through the manipulating assembly 50 which rotates drive member 13 with respect to clamp 9. As drive member 13 rotates, it causes inner bore 14 of clamp 9 to constrict. Once drive member 13 has been sufficiently tightened the constriction of inner bore 14 creates a clamping force which holds clamp 9 in the desired position on anchor head 45 of the bone anchor 7. Alternatively, the anchor head 45 may have an outer thread which would mate with threads inside the drive member 13 directly without the use of a collet. When drive member 13 is tightened, the unthreaded portion of anchor head 45 (which in this alternative arrangement is wider than inner bore 14) will be pulled against clamp 9 to fix their relative position. The bone anchor extension member 300 is then removed from the bone anchor 7. A torque is applied to the extension member 300 which disengages the threads 301 from the threads 12. Once the threads 301 and 12 are disengaged the extension member 300 can be removed. The stop member 311 is smaller than the inner bore 14 and therefore can slide through clamp 9 for removal if stop member 311 is still within the inner bore 14 once the clamp 9 has been reduced and fixed in position to the bone anchor 7.

Figure 4A:
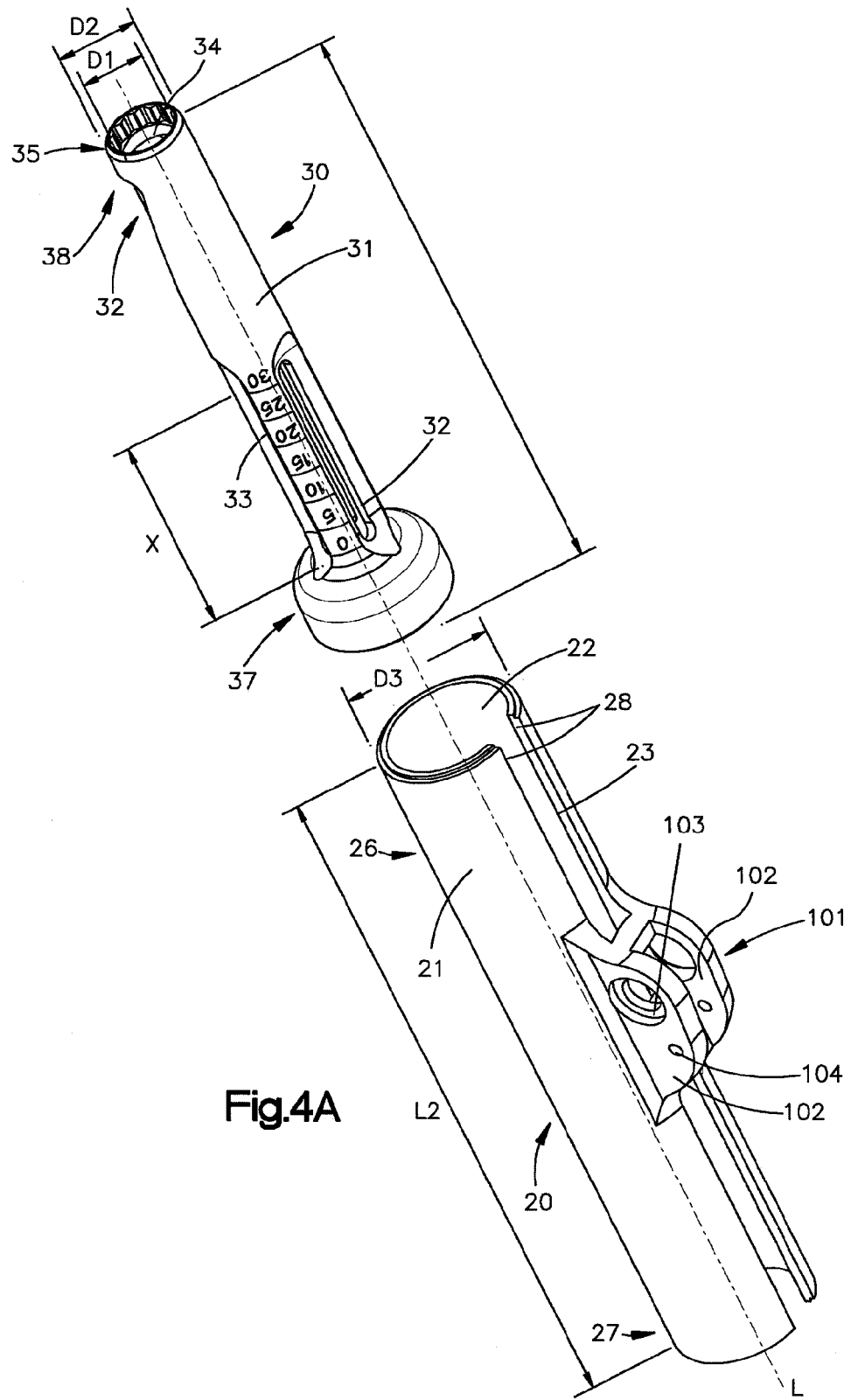
FIG. 4A is a perspective view of the housing and the socket assembly illustrated in FIG. 2.

Referring now to FIGS. 4A-B, the socket assembly 30 includes a socket shaft 31 which is a tubular member that extends from a distal end 38 to a proximal end 37 along the central longitudinal axis L, and defines a longitudinal length L1. The socket shaft 31 may be round in cross-section to allow for easier insertion in a small surgical workspace and to provide maximum visibility at the surgical site to a surgeon, but other tubular shapes, squared, triangular, etc., would also provide the stated functionality. The socket shaft 31 defines an inner bore 34 that extends through the entire length L1 of socket shaft 31.

The socket shaft 31 defines an inner diameter or cross-sectional dimension D1 that extends through the inner bore 34 along a direction perpendicular with respect to the longitudinal axis L. The diameter D1 is at least large enough along its entire length L1 to allow the bone anchor extension member 303 to pass through the inner bore 34 of socket shaft 31. The bone anchor extension members 300 are available in various sizes but typically range in diameter from about 3 mm to about 6 mm. The socket shaft 31 also defines an outer diameter or cross-sectional dimension D2 that extends along a direction perpendicular with respect to the longitudinal axis L. The outer diameter D2 may be constant or variable along the longitudinal axis L, but it is greater than D1. A thickness T is defined by the socket shaft, measured from an exterior surface 41 to an interior surface 42 perpendicular to the longitudinal axis L.

The socket shaft 31 includes a drive member 35 at its distal end 38. The drive member 35 is located within the inner bore 34 of socket shaft 31, and can be configured to correspond to the drive member 13 of the clamp 9, such that the drive member 35 is configured to be fixed to the drive member 13 with respect to rotation. For example, if clamp 9 includes an external 12-point nut then drive member 35 would be an interior 12-point recess. Similarly, if clamp 9 included an internal hex nut then drive member 35 would be an external hex recess. Although described in terms of hex drives it should be understood that drive member 35 may include a shape corresponding to any other fastener that could be used to secure the clamp 9 to the bone anchor 7, including but not limited to: wing nuts, round screws, rivets, etc.

The socket 30 can include at least one recess 32 that extends radially or laterally through the socket shaft 31. Thus, the recess 32 defines a depth equal to thickness T and a length X measured parallel to the central longitudinal axis L. The recess 32 provides visibility into the interior of the inner bore 34. The length X of recess 32 may vary but is long enough to provide a view of the bone anchor extension member 300 as it advances through socket assembly 30. Additional recesses 32 can be provided in distal end 38 to provide visualization of the clamp 9 and the bone anchor 7 interface. Alternatively, a clear window or other structure that provides for visibility into inner bore 34 could be included in the socket shaft 31 to provide visual aid to the surgeon.

The socket 30 can further include depth indicators 33 spaced along the socket shaft 31 at a location adjacent the recess 32. The depth indicators 33 provide information to the surgeon regarding how far the bone anchor extension member 300 has advanced into the socket assembly 30. The depth indicators 33 may be numbers etched into or printed on socket shaft 31 which indicate their distance from distal end 38. Alternatively, depth indicator 33 may be a hash mark which corresponds to a similar mark on bone anchor extension member 300. The alignment of these marks may inform the surgeon that the desired position for the clamp 9 has been reached.

The proximal end 37 of the socket shaft 31 attaches the socket assembly 30 to the housing 20. The proximal end 37 can use any fastening method known in the art to attach to the housing 20. For example, the proximal end 37 may be threaded to engage with corresponding threads in the housing 20. Alternatively, proximal end 37 may be attached to the housing with a press fit or friction fit. Other alternatives include pins or other fastening devices or permanent attachment methods such as welding. The socket assembly 30 and housing 20 may also be integrally formed.

Referring to FIGS. 3B and 4A, in use, the threads 307 of the bone anchor extension member 300 are secured to the threads 12 of the bone anchor 7 which has been implanted in an underlying vertebra. Drive member 13 of clamp 9 is secured to drive member 35 of socket assembly 30. The proximal end 305 of the bone anchor extension member 300 is then passed longitudinally through the inner bore 14 of clamp 9 and into the inner bore 34 of the socket shaft 31. In accordance with the illustrated embodiment, the drive member 35 is an internal hex drive that corresponds in shape to the drive member 13 that is used to tighten the clamp 9 onto the bone anchor 7. Alternatively, the drive member 35 can be any shape corresponding to a fastener.

Still referring to FIG. 4A, the housing 20 of the surgical instrument 10 includes a housing body 21 and an inner bore 22 that extends longitudinally through the housing body 21. Housing body 21 is a tubular member that extends longitudinally between a distal end 26 and a proximal end 27, defining a longitudinal length L2. The housing body 21 may be round in cross-section to allow for easier insertion in a small surgical workspace and to provide maximum visibility at the surgical site to a surgeon, but other tubular shapes, squared, triangular, etc., would also provide the stated functionality. The inner bore 22 defines an inner diameter or cross-sectional dimension D3 along a direction perpendicular with respect to the longitudinal axis L. The housing body 21 is configured to be coupled to, and in particular to receive, the gripping assembly 70 (shown in FIG. 3C). In particular, the diameter D3 is sized greater than the gripping assembly 70, such that the gripping assembly 70 can fit and slidably move within inner bore 22 along the longitudinal axis L.

The housing body 21 defines a gap 23 which allows access to the inner bore 22 of the housing body 21. Gap 23 can be defined by two opposing ends 28 of the housing body 21 that are circumferentially spaced, and provides open access from outside housing body 21 to inner bore 22. The size and shape of gap 23 can vary to accommodate the structure of the gripping assembly 70 and the reduction assembly 100 which can engage each other. In accordance with the illustrated embodiment, the gap 23 is a slot that runs the length L2 of the housing body 21. Alternatively, gap 23 may be absent from housing 21 which can enclose the gripping assembly 70 completely. In use, the distal end 26 of the housing is connected to the proximal end 37 of the socket assembly 30 and the proximal end 27 is connected to the manipulating assembly 50.

Referring now to FIG. 5, the manipulating assembly 50 includes a manipulating body 51. The manipulating body 51 is illustrated as a shaft member that defines a proximal end 55 and a longitudinally opposed distal end 56. The distal end 56 of the manipulating assembly 50 is sized and shaped such that it can be received by and rotatably fixed to proximal end 27 of the housing body 21 which it is connected to. The coupling of manipulating assembly 50 to housing body 21 can be accomplished as illustrated with proximal end 27 of housing body 21 being smaller than distal end 56 of manipulating assembly 50. The distal end 56 as illustrated is tubular, and can be threaded either internally or externally so as to engage corresponding threads of the housing body 21. Alternatively, the distal end 56 can be a solid plug, sized to fit within inner bore 22. Another alternative structure for distal end 56 is an end cap that fits over housing body 21. Yet another alternative includes manipulating assembly 50 being integrally formed as part of housing 20. Proximal end 55 includes a shaft 62 that is connected to distal end 56 and is aligned with central longitudinal axis L. The proximal end 55 may include a torque member 60. Torque member 60 may be an extension of shaft 62 or alternatively, torque member 60 may be a separable component joined to shaft 62 at a coupling 57. The coupling 57 serves to rotationally lock the torque member 60 with respect to shaft 62 and distal end 56. Thus, the coupling 57 can include corresponding engagement drives on the shaft 62 and torque member 60. One example of corresponding engagement drives would be an internal hex and an external hex. Coupling 57 may also include a built in torque limiter (not shown) which prevents over tightening of the clamp 9 when being fixed to the bone anchor 7. Accordingly, the torque member 60 is rotatably coupled to the distal end 56, such that a rotational biasing force applied to the torque member 60 is transferred to the distal end 56.

Torque member 60 may be a T-handle 61. T-handle 61 is sized to allow a surgeon's hand to grab and apply a torque to the manipulating assembly 51. Alternatively, torque member 51 can be any structure or handle suitable for a surgeon to grab and apply a torque to such as but not limited to a knob, crank, protrusion, etc.

Figure 6:
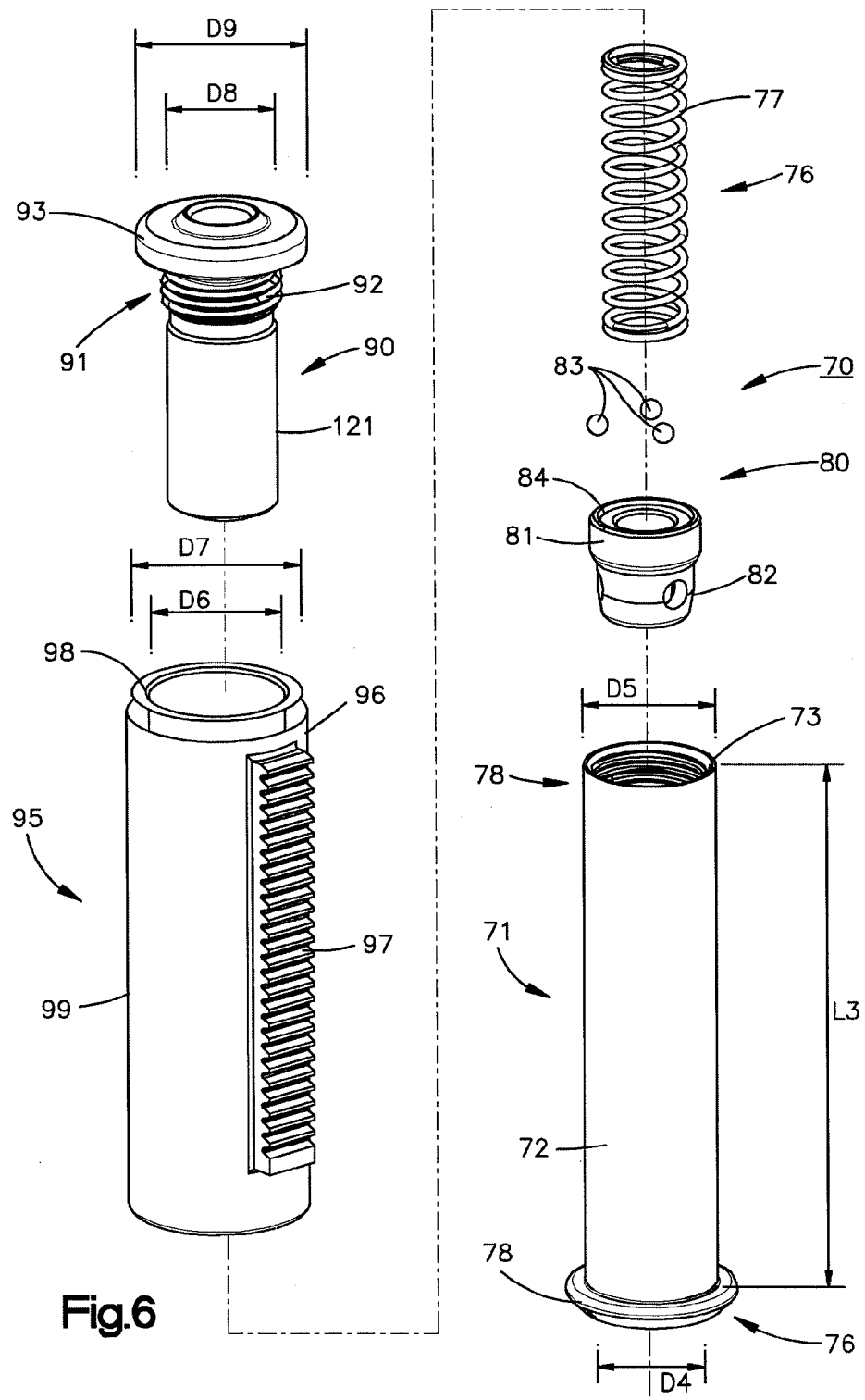
FIG. 6 is a side elevation view of the components of the gripping assembly illustrated in FIG. 2 constructed in accordance with one embodiment.
Figure 7A:
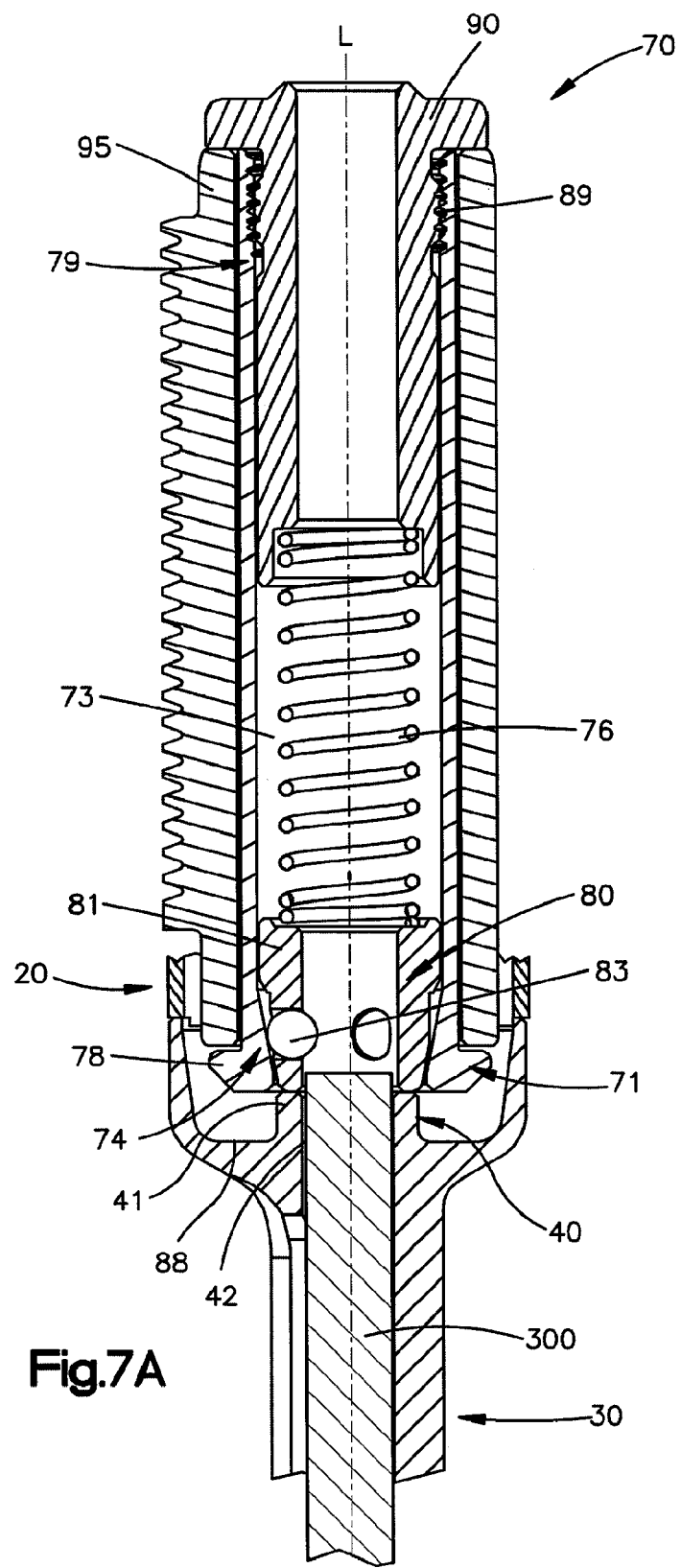
FIG. 7A is a magnified cross-section view of the gripping assembly illustrated in FIG. 3C in a first position before the gripping assembly has engaged the bone anchor extension member.

Referring now to FIGS. 6 and 7A, the gripping assembly 70 includes a sleeve 71, a biasing member 76, a ball bearing assembly 80, a rack member 95 and a sleeve cap 90. The sleeve 71 is a tubular member that defines a distal end 76 and an opposed proximal end 79 spaced from the distal end 76 along the longitudinal axis L, defining a length L3. The shape of the sleeve 71 may match that of housing body 21. For example, if the housing body 21 is circular then sleeve 71 may be circular as well but a smaller size so that it fits within the housing body 21. The Sleeve 71 has an inner bore 73 that extends through the entire length L3 of sleeve 71. The inner bore 73 defines an inner diameter or cross-sectional dimension D4, and an outer shell 72 of the sleeve 71 likewise defines an outer diameter or cross-sectional dimension D5. The inner diameter D4 is sized to be at least large enough to allow ball bearing assembly 80 to fit and slidably move longitudinally within inner bore 73. Sleeve 71 has a tapered portion 74 at its distal end 76. The inner diameter D4 thus decreases along a longitudinal direction toward the distal end 76. The outer diameter D5 is sized to fit within the inner bore 22 of the housing body 21. The outer diameter D5 can be substantially constant along the length L3, except for distal lip 78. As illustrated, at distal lip 78 D5 undergoes a step increase. Alternatively D5 can begin a tapered increase at distal lip 78. Distal lip 78 is illustrated as a protrusion in the outer shell 72 which provides a stop for the rack member 95 which receives the sleeve 71 such that the sleeve 71 is longitudinally slidable within the rack member 95.

The ball bearing assembly 80 includes a ball bearing housing 81 having at least one recess 82 and a locking member in the form of ball bearings 83 that are circumferentially disposed in each recess 82. The ball bearing housing 81 is a tubular member that has a length less than the length L3 of the sleeve 71. The shape of ball bearing housing 81 may match that of sleeve 71 such that the sleeve 71 is configured to receive the ball bearing housing 81. For example, if sleeve 71 is circular then ball bearing housing 81 may be circular as well but a smaller size so that it fits within inner bore 73 of sleeve 71. The ball bearing housing 81 has an inner bore 84 that extends through the entire ball bearing housing 81 along the longitudinal axis L. The ball bearing housing 81 may include one or more recesses 82. These recesses 82 are round and are sized to accommodate the ball bearing 83. The recess 82 is a circular opening in ball bearing housing 81 which goes through the thickness of the ball bearing housing 81 such that it allows the ball bearing 83 access to both the interior and exterior of ball bearing housing 81 at the same time. For example, the ball bearing 83 housed in the recess 82 may simultaneously contact both the interior surface of the sleeve 71 and the exterior surface of the bone anchor extension member 300 that is positioned within inner bore 84 of the ball bearing housing 81. The ball bearing housing 81 may contain three ball bearings 83, each spaced circumferentially apart 120 degrees. Alternatively, it will be appreciated by one of ordinary skill in the art, the ball bearing housing 81 may include more or less ball bearings 83 circumferentially spaced at different intervals.

The biasing element 76 also slidably fits within the inner bore 73 of the sleeve 71. The biasing element 76 can be any compressible structure or material that is sized and shaped to fit within inner bore 73. One such biasing element is a compression spring 77 with an outer diameter less than D4. Alternatively, biasing element 76 may be absent and gravity may supply the biasing force instead.

Figure 8A:
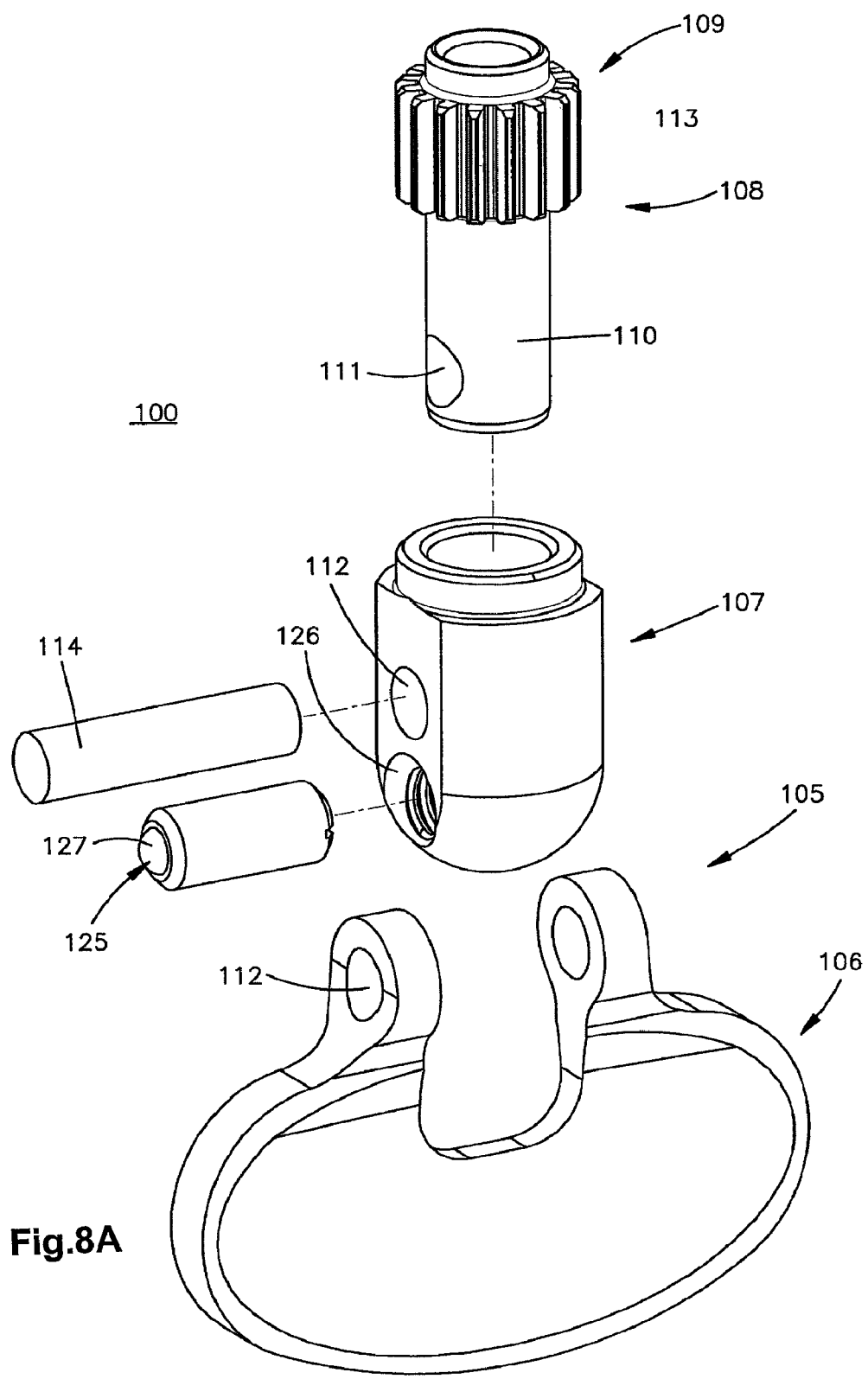
FIG. 8A is a perspective view of the reduction assembly illustrated in FIG. 2 constructed in accordance with one embodiment including a gripping member, a bearing, a pinion, a pin and a ball plunger.

The rack member 95 is illustrated as a tubular body 99 that defines a longitudinal length L4 with a shape that can match that of housing body 21 such that the rack member 95 can be received in the inner bore 22 of the housing body 21. For example, if housing body 21 is circular then rack member 95 may be circular as well but sized smaller than the housing body 21. The rack member 95 defines an inner bore 98 that extends through the entire length L4 of the rack body 99 along the longitudinal axis L. The inner bore 98 defines an inner diameter or cross-sectional dimension D6 along a direction perpendicular with respect to the longitudinal axis L. The diameter D6 can be constant and sized larger than the diameter D5 of the sleeve 71 that is received in the bore 98 of the rack body 99. The rack body 99 defines an outer surface 96 that defines an outer diameter or cross-sectional dimension D7 of rack member 95 that extends along a direction perpendicular to the longitudinal axis L. The outer diameter D7 is sized smaller than D3 of the housing body 21 so that rack member 95 can slidably move within inner bore 22 of housing body 21. The rack member 95 further comprises a rack 97 or other drive feature carried by the rack body 99. The rack 97 is configured to engage teeth 113 or another driving portion 109 of a pinion 108 (see FIG. 8). The rack 97 is positioned on the outer surface 96 of the rack body 99, and extends parallel to the longitudinal axis L.

The sleeve cap 90 secures the rack member 95 to the sleeve 71. The sleeve cap 90 includes an engagement section 91 that secures the sleeve cap 90 to the sleeve 71, and an outwardly projecting proximal lip 93. The engagement section 91 can be provided as a tubular body 121 that has a shape that corresponds to the sleeve 71 to allow engagement section 91 to engage the sleeve 71. The engagement of body 121 to tapered sleeve 71 is a releasable coupling. The engagement section 91 defines an outer diameter or cross-sectional dimension D8 which is less than inner diameter D6 of rack member 95, such that the rack member body 99 is configured to receive the engagement section 91. The engagement section 91 can have external threads 92 that are configured to engage corresponding threads 89 on the interior of the proximal end 79 of the sleeve 71. Alternatively, the engagement section 91 can be a solid plug, sized to fit within the inner bore 73 of the sleeve 71. It should be appreciated that the engagement section 91 can alternatively include any type of fastener configured to releasably join the engagement section 91 and the sleeve 71 such as but not limited to: interference fittings, pins, and the like. The proximal lip 93 is illustrated as a disc member that extends out from the engagement section 91 along a direction perpendicular to the longitudinal axis L. The proximal lip 93 defines an outer diameter or cross-sectional dimension D9 which is greater than the outer diameter D7 of the rack member 95. Thus, once sleeve cap 90 has been secured to sleeve 71, the rack member 95 is captured securely in place, relative to sleeve 71, between the distal lip 78 of the sleeve 71 and the proximal lip 93 of the sleeve cap 90. Alternatively, sleeve cap 90 could be integral with rack member 95.

Figure 7B:
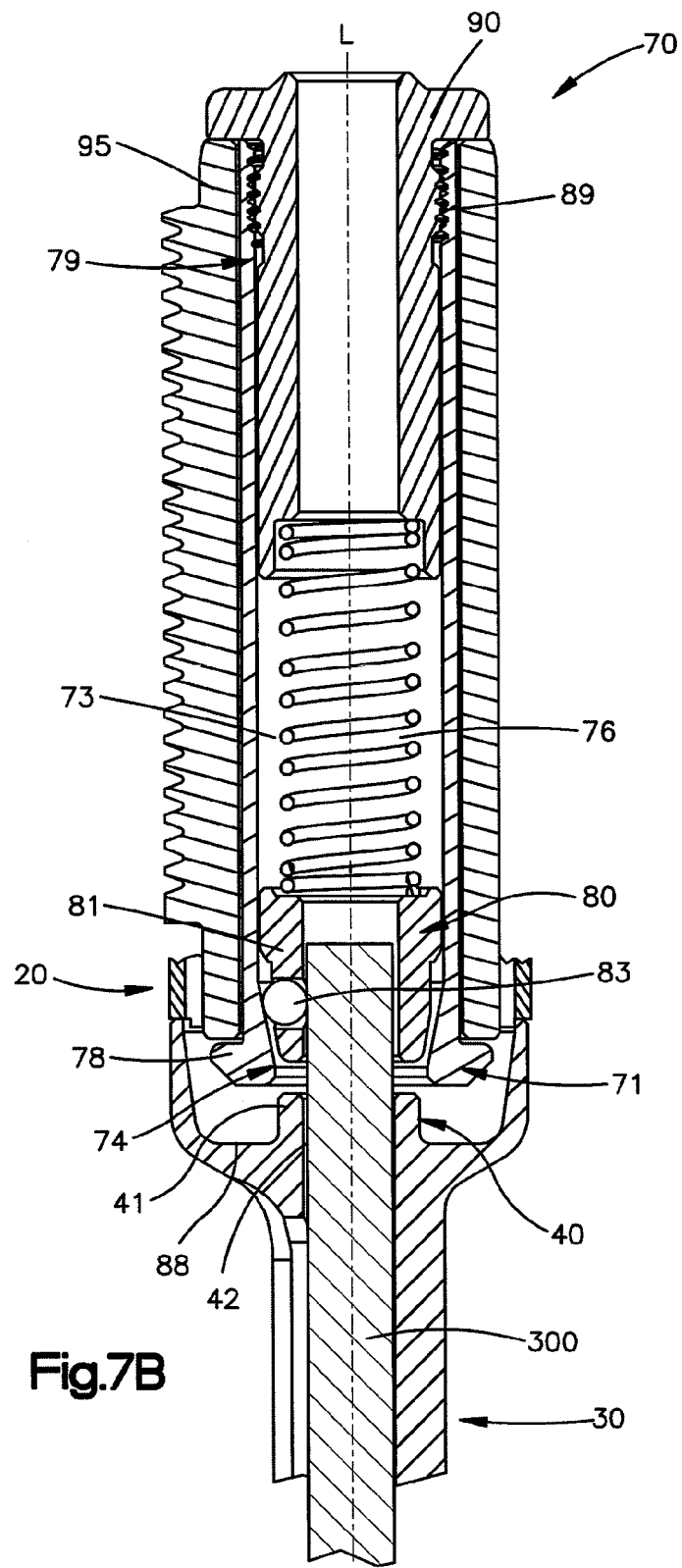
FIG. 7B is a magnified cross-section view of the gripping assembly illustrated in FIG. 3C in a second position in which the gripping assembly has engaged the bone anchor extension member.
Figure 7C:
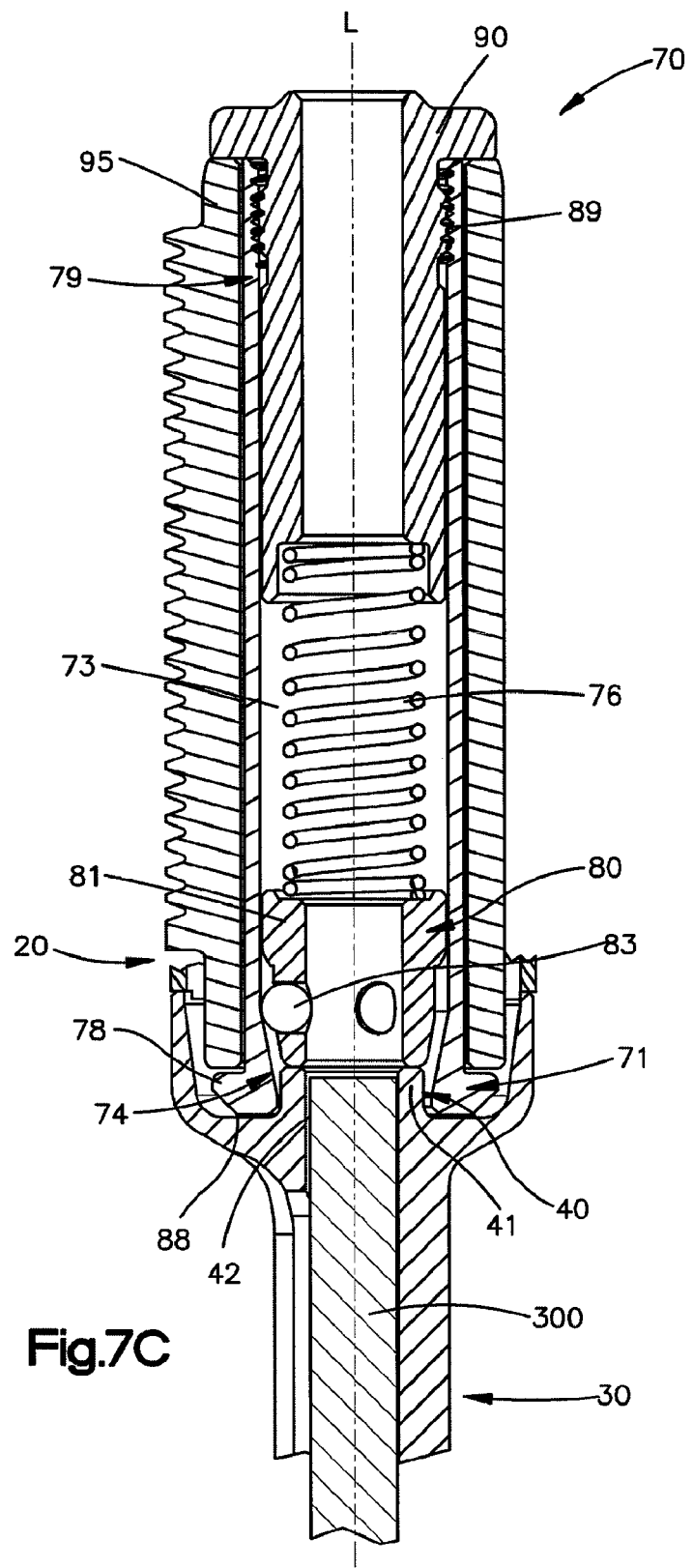
FIG. 7C is a magnified cross-section view of the gripping assembly illustrated in FIG. 3C in a third position in which the gripping assembly has released the bone anchor extension member.

Referring now to FIGS. 7A-C, the proximal end of the bone anchor extension member 300 is inserted longitudinally into the inner bore 34 of the socket assembly 30. As the extension member 300 passes into the housing 20 it enters the inner bore 73 of sleeve 71. The extension member 300 is brought into contact with the ball bearing assembly 80 (see FIG. 7A). As the extension body 303 is advanced further into the surgical instrument 10 the ball bearing assembly 80 is forced back toward the proximal end 27 of the housing 20 against the force of the compression screw 76. As the ball bearing assembly 80 advances proximally within the inner bore 73, the inner bore 73 widens along the tapered portion 74 of the sleeve 71. Thus, as the ball bearing assembly 80 advances proximally (toward proximal end 79 of sleeve 71) the tapered portion 74 provides the ball bearings 83 with increasing room to spread apart. Eventually the ball bearings 83 will be far enough apart to define a bore that allows the extension body 303 to pass through freely in the proximal direction (see FIG. 7B). Conversely, the ball bearing assembly 80 can advance distally such that the ball bearings 83 ride toward each other as they travel distally along the tapered portion, until the ball bearings 83 lock against the extension body 303, thereby coupling the ball bearing assembly 80 to the extension member 300.

Referring again to FIG. 3C, the housing 20 can include a stop 130 that is disposed within the housing body 21. The stop 130 is illustrated as a longitudinally extending shaft that is disposed inside the inner bore 22 of housing body 21. The stop 130 includes a proximal end 131 and a longitudinally opposed distal end 132. The proximal end 131 is attached to the manipulating assembly 50. The distal end 132 extends into the inner bore 22 of housing body 21. The stop 130 can have an appropriate length to limit the depth to which the bone anchor extension member 300 can enter surgical instrument 10. The bone anchor extension member 300 advances proximally into the inner bore 34 of socket assembly 30 and then into inner bore 22 of housing 20 until the extension member 300 contacts the distal end 132 of the stop 130, thereby limiting any further proximal movement of extension body 303 within housing body 21.

Referring again to FIGS. 7A-C, as the reduction assembly 100 is operated, a force is applied to rack member 95 which results in gripping assembly 70 moving proximally relative to extension body 303. This results in the ball bearings 83, due to friction and the light spring force applied by the coiled compression spring 77, being pulled tighter or distally with respect to the sleeve 71 resulting in the ball bearings 83 gripping the extension member 300 in the manner described above. This arrangement allows the gripping assembly 70 to work with a range of various bone anchor extension members 300 of different sizes, shapes and surfaces.

Further longitudinal movement of the bone anchor extension member 300 in the distal direction relative to the gripping assembly 70 is prevented by interference between the ball bearing assembly 80 and the tapered portion 74 of the sleeve 71. In particular, as the bone anchor extension member 300 attempts to move distally, the tapered portion 74 causes the ball bearings 83 to pinch in on the bone anchor extension member 300. Thus, when a force is applied to the gripping assembly 70 by the reduction assembly 100, the housing 20 and socket assembly 30 (with an attached clamp 9) are moved toward the bone anchor 7.

The reduction assembly 100 will now be described with respect to FIGS. 8A-C and 9. In particular, the reduction assembly 100 includes a frame 101 either integrally or discreetly attached to the housing 20. The reduction assembly 100 further includes a handle 105 and a pinion 108 carried by the frame 101. The frame 101 includes two parallel, opposing tabs 102 (see FIG. 4A). Each tab 102 is a plate type structure and is attached to the housing 20 on either side of the gap 23, such that the gap 23 is disposed between the tabs 102. The reduction assembly can also include at least one aperture 103 extending through the tabs 102. In particular, each aperture 103 extends completely through the respective recess 103 in a direction perpendicular to longitudinal axis L. The tabs 102 are configured to support the handle 105 and the pinion 108, as will now be described.

Referring to FIGS. 3A, 4 and 8, pinion 108 is disposed between the tabs 102, and the handle 105 is coupled to the pinion 108 such that the handle 105 is rotatable with respect to the pinion 108. The pinion 108 includes a driving portion 109 which has teeth 113 which mesh with the rack 97 on rack member 95 (see FIG. 3C). The driving portion 109 of pinion 108 is positioned between the tabs 102 so as to restrict lateral movement of pinion 108. The pinion 108 also has a shaft 110 which extends from the driving portion 109 through one of tabs 102. A portion of shaft 110 extends through first aperture 103 of frame 101 and includes a recess 111. Recess 111 is aligned with a corresponding recess 112 in handle 105. A pin 114 inserted through aligned recesses 111 and 112 rotationally locks the handle 105 with pinion 108. Alternatively, handle 105 and pinion 108 may be joined by any other temporary or permanent means known in the art such as welding, set screws, etc. that allow the handle 105 and pinion 108 to be rotationally locked with respect to one another.

As illustrated, the handle 105 includes a gripping member 106 and a bearing 107. The gripping member 106 is a flat, disk member shaped to allow a surgeon to grip and apply a torque to the reduction assembly 100. The bearing 107 is a tubular member that receives the shaft 110 of the pinion 108 and is rotationally coupled to the gripping member 102. Gripping member 106 and bearing 107 may also be pivotally connected, such as by a pin 114, to allow gripping member 106 to be pivoted against housing 20. The handle 105 may contain a ball plunger 125 which releasably connects the gripping member 106 with the bearing 107 to maintain the optimal alignment for applying torque to the pinion 108. Ball plunger 125 is received by a recess 126 in the bearing 107 before pivotally connecting the gripping member 106 with the bearing 107. When the ball plunger 125 is fully inserted into the recess 126 only a nose 127 protrudes from the recess 126. The nose 127 releasably contacts the gripping member 106 and provides a force which keeps the gripping member properly aligned with the bearing 107. Referring to FIG. 8B, gripping member may include a divot 128 which releasably engages with nose 127. Divot 128 is a concave indent into the gripping member 106. If the surgeon wishes to pivot the gripping member 106 out of the way, the force provided by the nose 127 must be overcome. The embodiment of the reduction assembly 100 as described above is shown assembled in FIG. 8C.

Figure 9:
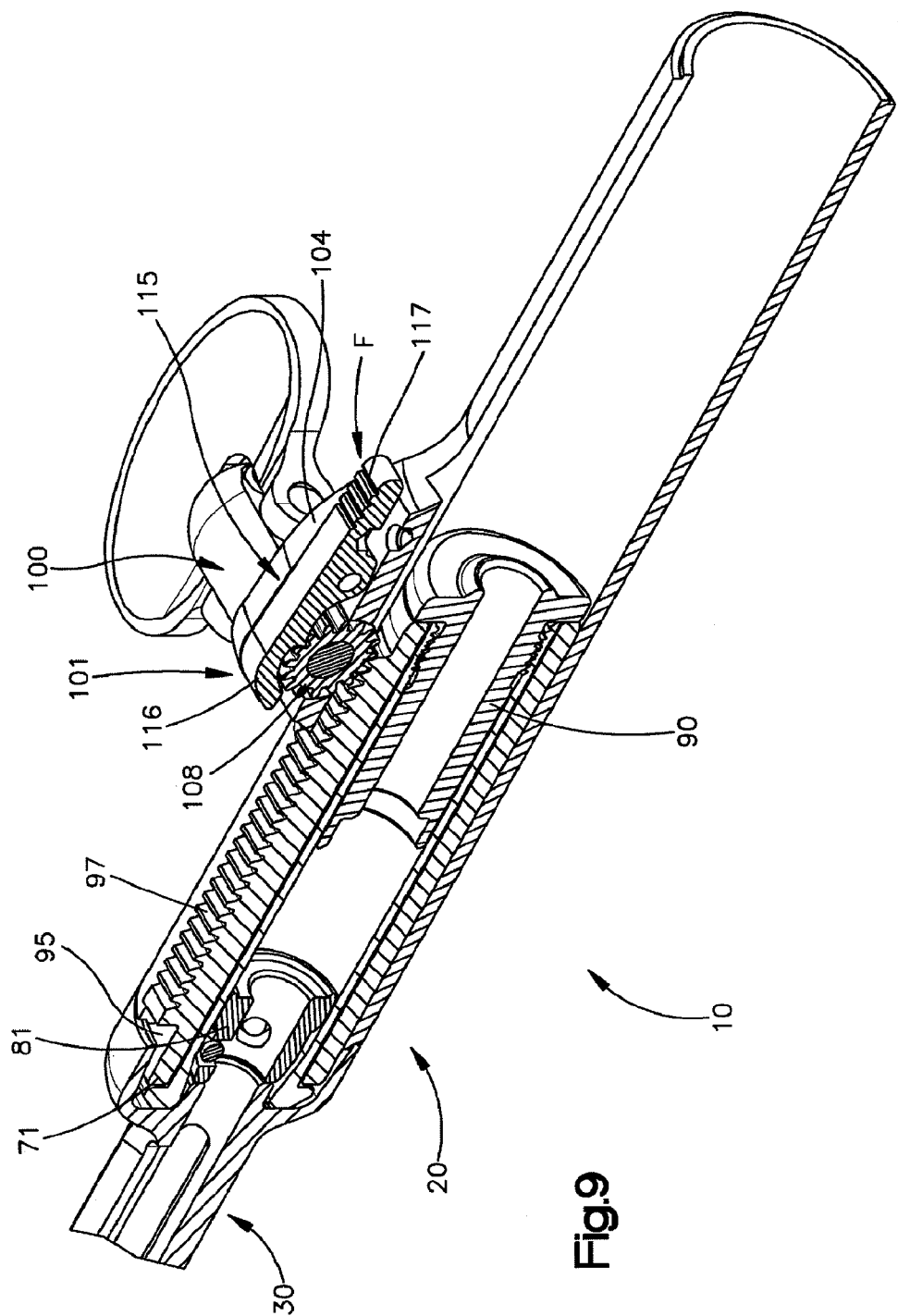
FIG. 9 is a magnified cross-section view of the gripping assembly and reduction assembly illustrated in FIG. 3C
Figure 10:
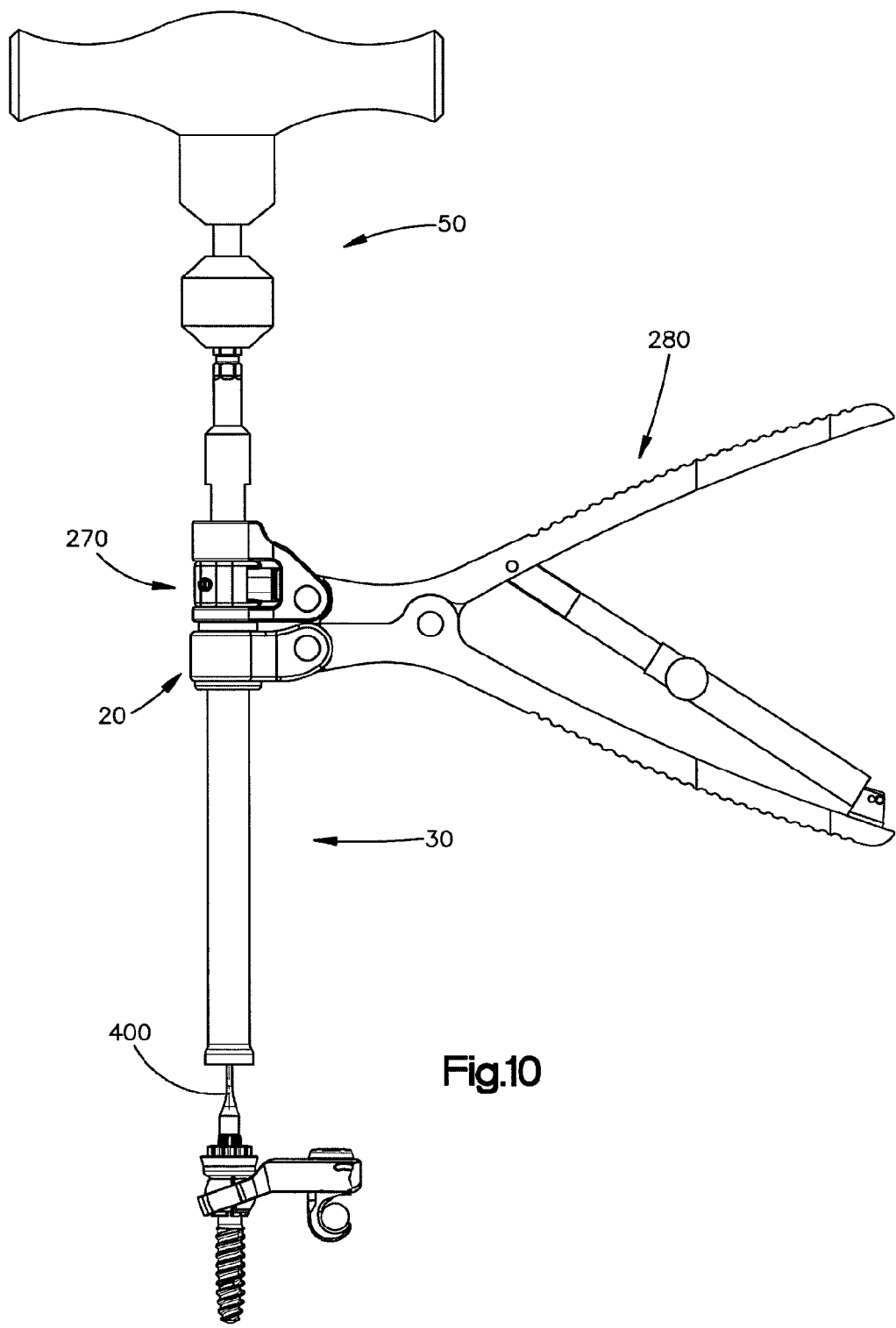
FIG. 10 is a side elevation view of a surgical instrument constructed in accordance with another embodiment including a housing, a socket assembly, a manipulating assembly, a gripping assembly and a reduction assembly, showing the surgical instrument engaged with an extension member that is connected to a bone fixation device.
Figure 11:
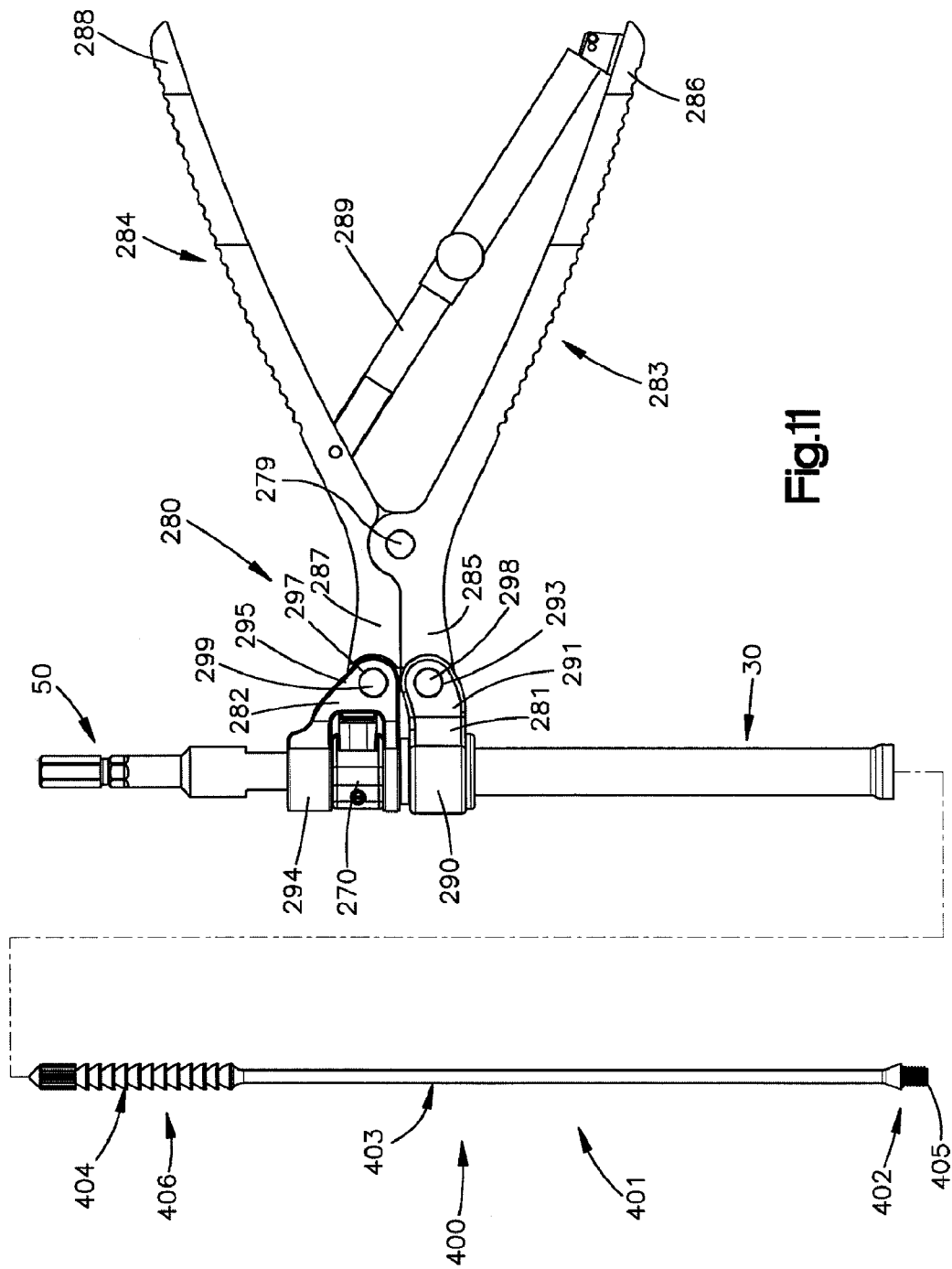
FIG. 11 is side elevation view of the surgical instrument and extension member illustrated in FIG. 10.
Figure 12A:
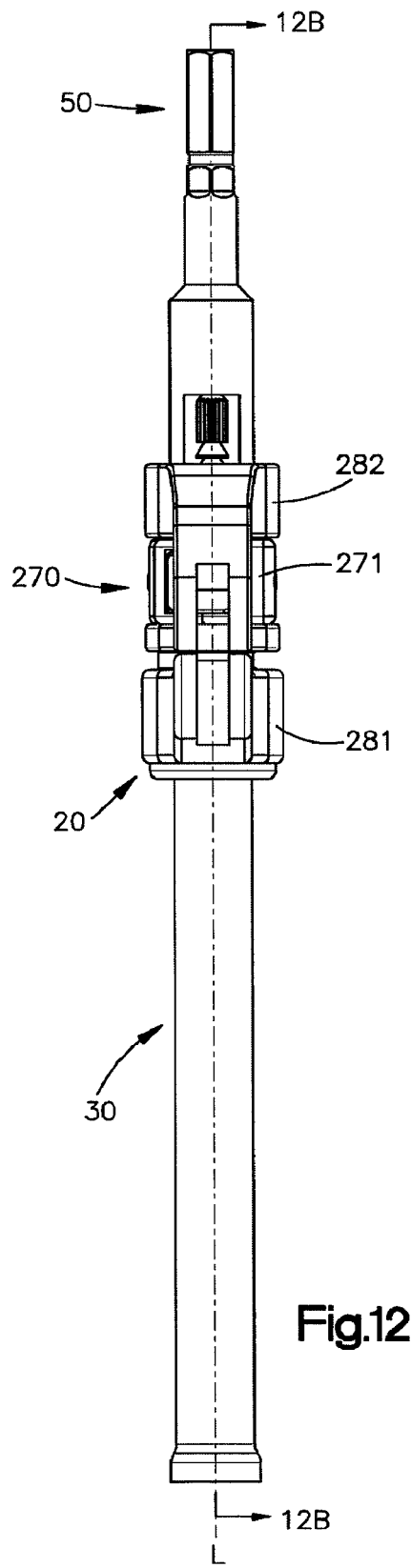
FIG. 12A is a top elevation view the surgical instrument and extension member illustrated in FIG. 11, the surgical instrument including a housing, socket assembly, manipulating assembly, gripping assembly, and reduction assembly.
Figure 12B:
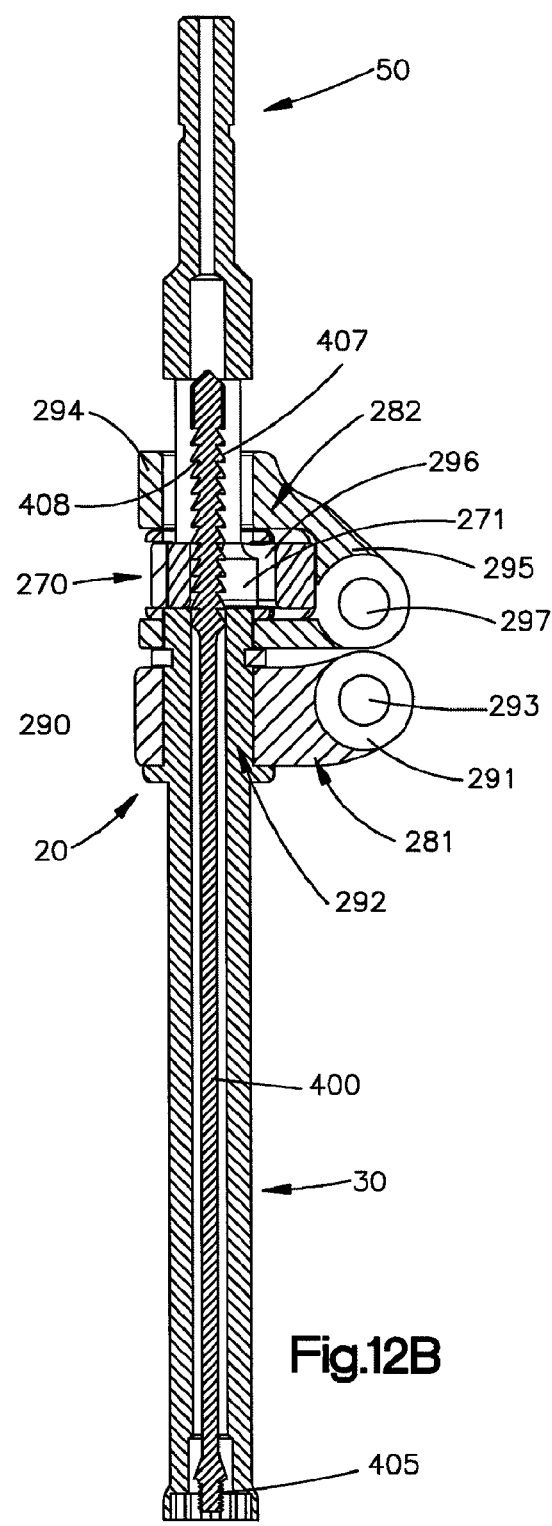
FIG. 12B is a cross-sectional view of the housing, socket assembly, manipulating assembly, gripping assembly and reduction assembly engaged with the extension member along line 12B-12B of FIG. 11.

Referring to FIG. 9, the reduction assembly 100 may additionally include a catch 115. Catch 115 is a shaft member which has a stopper end 116 and a release end 117 and is pivotally connected to frame 101. A pin 118 inserted through second recess 104 (see FIG. 4A) in tab 102 and through a recess 119 in catch 115 is one alternative for pivotally connecting the catch 115 to the frame 101 and thus the rest of surgical instrument 10. The stopper end 116 of catch 115 engages with pinion 108 and prevents rotational movement of the pinion in one direction. A force applied in direction F to release end 117 will cause stopper end 116 to disengage with pinion 108 and pinion 108 is then able to rotate in both directions.

After the gripping assembly 70 has been secured to the extension body 303, a surgeon can apply a torque to handle 105, thereby causing the handle 105 and the pinion 108 to rotate together. The teeth 113 of pinion 108 engage with rack 97 of rack member 95 and apply a biasing force to rack 97 along the longitudinal axis L of the surgical instrument 10. Due to the gripping assembly 70 being locked to the extension body 303 such that distal movement of the extension body 303 relative to the gripping assembly 70 is prevented, the force along the longitudinal axis L of surgical instrument 10 causes the housing 20 and socket assembly 30 to move distally with respect to the gripping assembly 70. The longitudinal movement of the housing 20 and the socket assembly 30 allows the clamp 9 or other fixation device held within drive member 35 to be positioned in the desired location on the bone anchor 7.

The surgical instrument 10 may include a low friction coating as desired to facilitate longitudinal sliding of the various components. The interface between the ball bearing housing 80 and the rack member 95 is one area of sliding that may benefit from a low friction coating. The use of ball bearings 83 also reduces friction and may negate the need for a low friction coating. One method of applying the low friction coating is via a Plasma Vapor Deposition process. The coating reduces the associated friction during tightening of the clamp 9 while pulling on the bone anchor 7. In one embodiment the sleeve cap 90 and the rack member 95 are coated with a low friction coating deposited via a Plasma Vapor Deposition process. The low friction coating coupled with the ball bearings 83 allow the surgical instrument 10 to pull on the bone anchor extension member 300 and push on the clamp 9, isolating the forces from the patient's body.

Referring again to FIGS. 3A and 9, to release the extension body 303 from the gripping assembly 70, first the release end 117 of the catch 115 is pressed to disengage the stopper end 116 from pinion 108. The pinion 108 is now free to rotate in both directions. The housing biasing member 120 provides a force against the gripping assembly 70 and moves the entire gripping assembly 70 toward the distal end 26 of housing 20. Housing biasing member 120 slidably fits within the inner bore 22 of the housing body 21. The housing biasing member 120 can be any compressible structure or material that is sized and shaped to fit within inner bore 21. One such biasing element is a compression spring 121 with an outer diameter less than D3. As reduction assembly 100 causes housing 20 to translate with respect to gripping member 70, housing biasing member 120 is compressed.

Referring to FIG. 7C, a ball bearing riser 40 is included as part of the socket assembly 30. Alternatively the ball bearing riser 40 can be included as a part of the distal end 26 of the housing 20. The ball bearing riser 40 is a tubular member with a shape that is received by the inner bore 73 of sleeve 71. Ball bearing riser 40 includes a post 41, an inner bore 42 that extends longitudinally through the post 41, and a sleeve stop 88. The inner bore 42 has a diameter or cross-sectional dimension that is large enough so as to receive the extension member 300 such that the extension member 300 is longitudinally translatable within the bore 42. The post 41 is a tubular member that defines an outer diameter D10 that is less than inner diameter D4 such that sleeve 71 can pass over ball bearing riser 40 without interference. Sleeve stop 88 is a circular stop that surrounds post 41. Sleeve stop 88 is sized to receive distal lip 78 of sleeve 71.

When the catch 115 is disengaged from the pinion 108, the housing biasing member 120 expands within the inner bore 22 along the longitudinal axis L. As the housing biasing member 120 expands it pushes the gripping assembly 70 toward the socket housing 30. Eventually, the ball bearing assembly 80 contacts the post 41 and it is prevented from moving any farther distally with the rest of the gripping assembly 70. However, the sleeve 71, the rack member 95 and the sleeve cap 90 are still free to move distally within the inner bore 22. The sleeve 71, rack member 95 and sleeve cap 90 continue to move distally until distal lip 78 contacts sleeve stop 88. This relative movement between the ball bearing housing 81 proximally within the inner bore 73 of the sleeve 71 allows ball bearings 83 to spread out in the larger diameter portion of inner bore 73. This releases the pinching force on the bone anchor extension member 300, thereby releasing the bone anchor extension member 300 from the ball bearings 83. The bone anchor extension member 300 can then be removed completely from surgical instrument 10.

Referring to FIGS. 10-13D the surgical instrument 10 is illustrated having the similar housing 20, socket assembly 30, and manipulating assembly 50 as described above. However, the surgical instrument 10 includes a gripping assembly 270 and a reduction assembly 280, each constructed in accordance with an alternative embodiment. In particular, the reduction assembly 280 includes a first attachment member 281, a second attachment member 282, a first gripping member 283 and a second gripping member 284. The first attachment member 281 is illustrated as a tubular body 290 and a tab portion 291 extending radially or laterally out from the body 290. The reduction assembly 280 further includes an inner bore 292 that extends through the body portion 290. The inner bore 292 is sized to receive the housing 20. The tab portion 291 extends away from the body portion 290 and can define a through hole 293 or other recess sized to accept a fastener that attaches the tab portion 291 to the first gripping member 283.

Similarly, the second attachment member 282 includes a tubular body 294 and a tab portion 295 that extends radially or laterally out from the body 294. The body portion 294 includes an inner bore 296 which is sized to receive the housing 20. The tab portion 295 extends away from the body 294 and can define a through hole 297 or other recess sized to accept a fastener that attaches the tab portion 295 to the second gripping member 284. The second attachment member 282 is attached to housing 20 at a location proximally of first attachment member 281.

The first gripping member 283 is illustrated as a shaft member which includes an output end 285 and an input end 286. The first gripping member 283 can be any shape that allows for a surgeon to grip and apply a force to the input end 286. The output end 285 defines a through hole 298 which is aligned with the through hole 293 of the first attachment member 281 so as to pivotally attach the output end 285 to the first attachment member 281. Likewise, the second gripping member 284 is a shaft member which includes an output end 287 and an input end 288. The second gripping member 284 can be any shape that allows for a surgeon to grip and apply a force to input end 288. The output end 287 contains a through hole 299 which is aligned with through hole 297 of the second attachment member 282 so as to pivotally attach output end 287 to the second attachment member 282. The first and second gripping members 283, 284 are pivotally coupled to each other at a location between their output ends 285, 287 and their input ends 286, 288. This pivotal coupling can be accomplished in one embodiment by a pin joint 279 that causes the output ends of the first and second attachment members 281, 282 to slide apart from each other along housing 20 when input ends 286, 288 are moved together. A linear ratchet 289 can be connected to the first and second gripping members 283, 284. The linear ratchet 289 serves to hold the reduction after the surgeon releases the first and second gripping members 283, 284. The linear ratchet 289 includes a release 278 which can be used to disengage the ratchet mechanism and release the reduction.

Figure 13A:
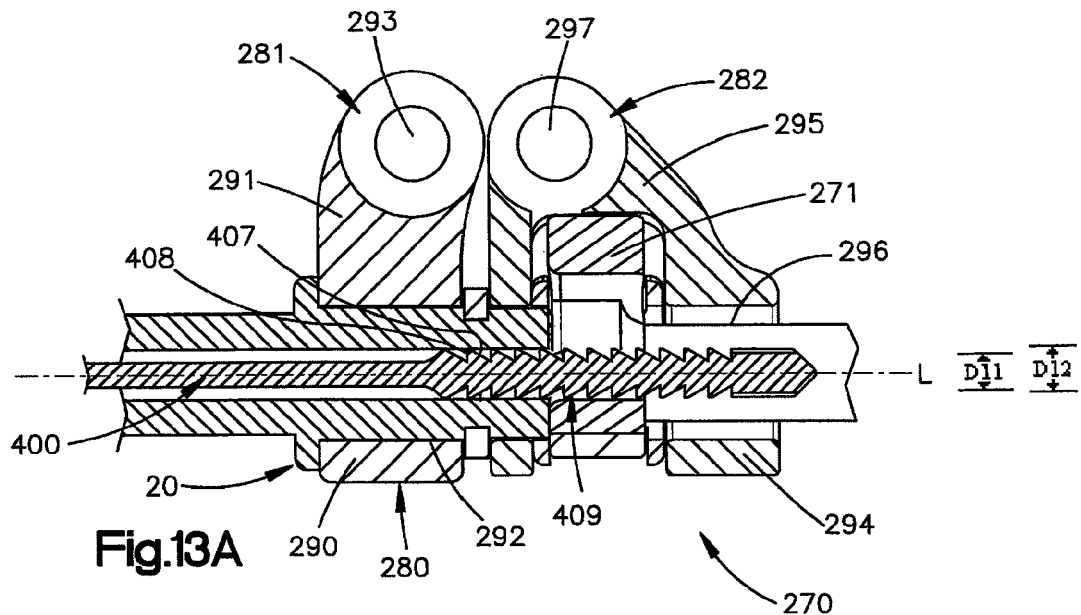
FIG. 13A is a cross-sectional view of the gripping assembly illustrated in FIG. 10 including an interference fitting and engaged with a bone anchor extension member.
Figure 13B:
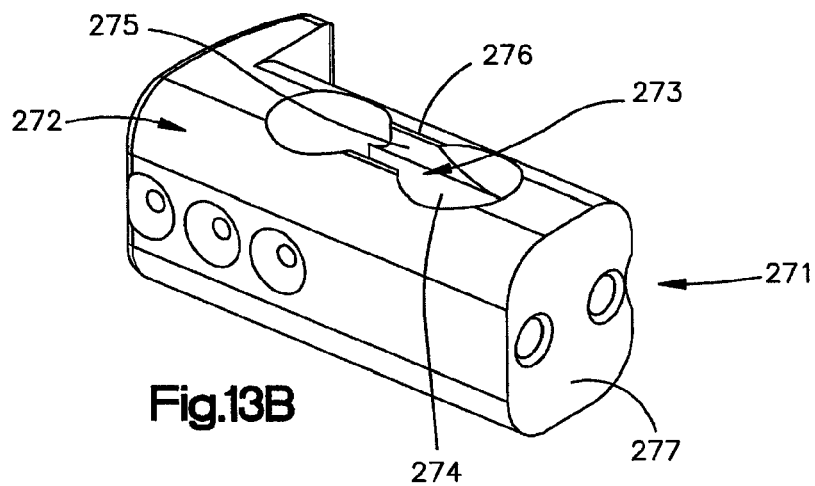
FIG. 13B is a perspective view of the interference fitting illustrated in FIG. 13A.
Figure 13C:
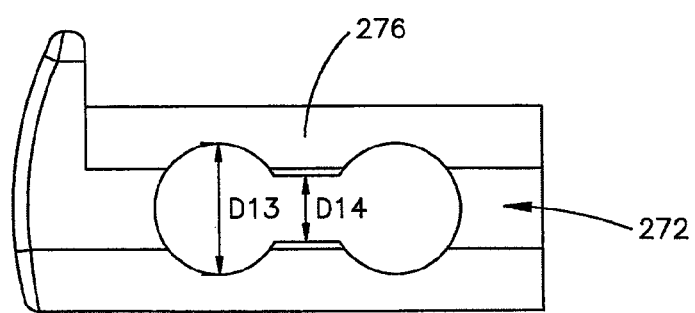
FIG. 13C is a front elevation view of the interference fitting illustrated in FIG. 13A.

The gripping assembly 270 is configured to engage with a bone anchor extension member 400 constructed in accordance with an alternative embodiment. In particular, the extension member 400 includes a shaft 401 that defines a distal portion 402, a longitudinally opposed proximal portion 404 and an intermediate portion 403 disposed between the proximal portion 404 and the distal portions 402. The extension member 400 includes threads 405 or alternative engagement feature carried by the distal portion 402 of the shaft 401 to secure the extension member 400 to the bone anchor 7. The intermediate portion 403 connects distal end 402 to proximal end 404. The proximal end 404 includes a segmented portion 406. The segmented portion 406 has a series of repeating tapers 409 with a sloped proximal surface 407 and a flat distal surface 408 as shown in FIG. 13. Each taper 409 defines a minimum outer diameter or cross-sectional dimension D11 and a maximum outer diameter or cross-sectional dimension D12. The diameters D11 and D12 may be constant throughout segmented portion 406. The diameter D12 is sized to fit and slidably move within housing 20. The bone anchor extension members 400 are available in various sizes but typically range in minimum outer diameter from about 3 mm to about 6 mm.

In accordance with the illustrated embodiment, the gripping assembly 270 includes an interference fitting 271 that is slidably attached to housing 20 and also is slidably coupled to the second attachment member 282. The interference fitting 271 is illustrated as a plate member that includes a body 272 with a recess 273. Body 272 is sized to slidably engage with housing 20 and can be any shape but it is desirable that the body correspond generally to the shape of housing 20 so as not to interfere with visibility of the surgical sight. The recess 273 extends through the entire body 272 along longitudinal axis L, and includes a pass-through portion 274 and a blocking portion 275. The pass-through portion 274 defines a diameter or cross-sectional dimension D13 which is larger than that of the blocking portion 275 which defines a recess D14. The diameter D13 of the interference fitting 271 is larger than the diameter D12 so as to allow bone anchor extension member 400 to slide through freely when the pass-through portion 274 is aligned with longitudinal axis L. The recess D14 is tapered and is smallest at a distal face 276 of the interference fitting 271 and greatest at a proximal face 277 of the interference fitting 271. At the distal face 276, the recess D14 is larger than the diameter D11 but smaller than diameter D12. Thus when blocking portion 275 is aligned with longitudinal axis L, the minimum outer diameter D11 is able to slide through interference fitting 271 but the maximum outer diameter D12 is stopped from sliding through interference fitting 271.

During operation, the extension screw 400 is engaged with a bone anchor 7 by engaging threads 405 with receiving threads 12 in bone anchor 7. The clamp 9 is engaged with the drive member 35 of socket assembly 30 and extension screw 400 is inserted through the socket assembly 30 of surgical instrument 10. The segmented portion 406 of extension member 400 is moved through the pass-through portion 274 of the interference fitting 271. The interference fitting 271 is then slid laterally to align the blocking portion 275 with the flat distal surface 408, thereby preventing the extension member 400 from backing out of the surgical instrument 10. As the input ends 286 and 288 are pushed together, the output ends 285 and 287 are pushed apart from each other, thereby also pushing the first and second attachment members 281 and 282, which are connected to the output ends 285 and 287, respectively, away from each other. The blocking portion 275 prevents the interference fitting 271 and extension member 400 from moving relative to each other. Since extension member 400 is attached to the anchored bone anchor 7, the first attachment member 271 and the housing 20 it is connected to are forced to move distally toward the bone anchor 7, thereby allowing the clamp 9 held within drive member 35 to be positioned in the desired location on the bone anchor 7. Once the clamp 9 is in the desired location, it can be secured by applying a torque through manipulating assembly 50 in the manner described above. The interference fitting 271 can then be slid laterally so as to align the pass-through portion 274 with the extension member 400, which thereby allows the extension member 400 to be freely removed from the surgical instrument 10. Then, the extension member 400 can be removed from the bone anchor 7.

Figure 15:
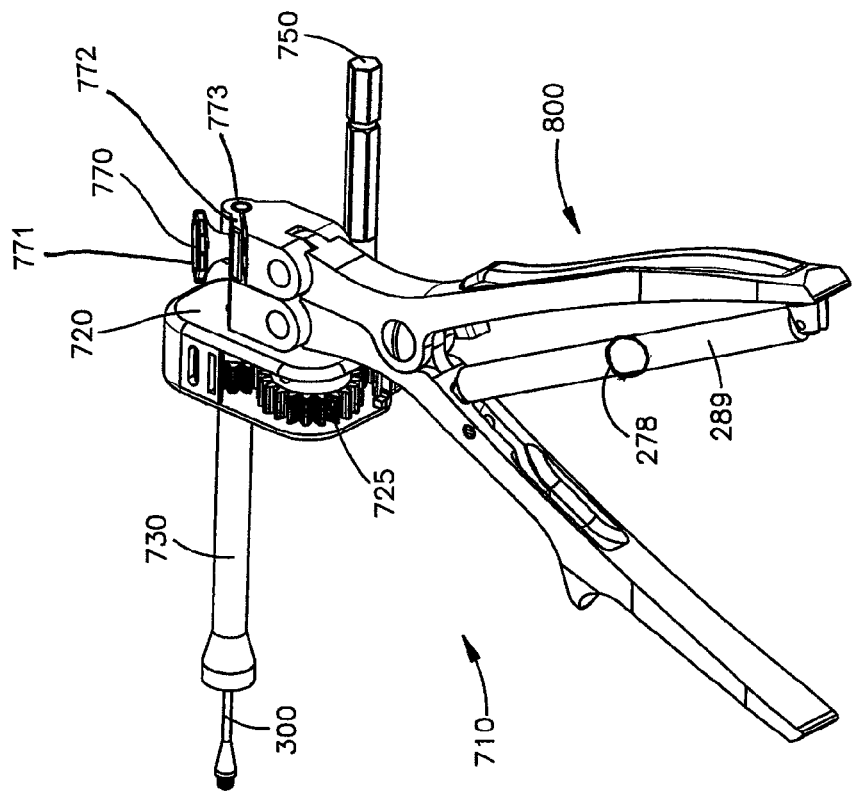
FIG. 15 is a perspective view of the surgical instrument constructed in accordance with another embodiment including a housing, a socket assembly, a manipulating assembly, a gripping assembly and a reduction assembly, showing the surgical instrument engaged with an extension member.
Figure 14:
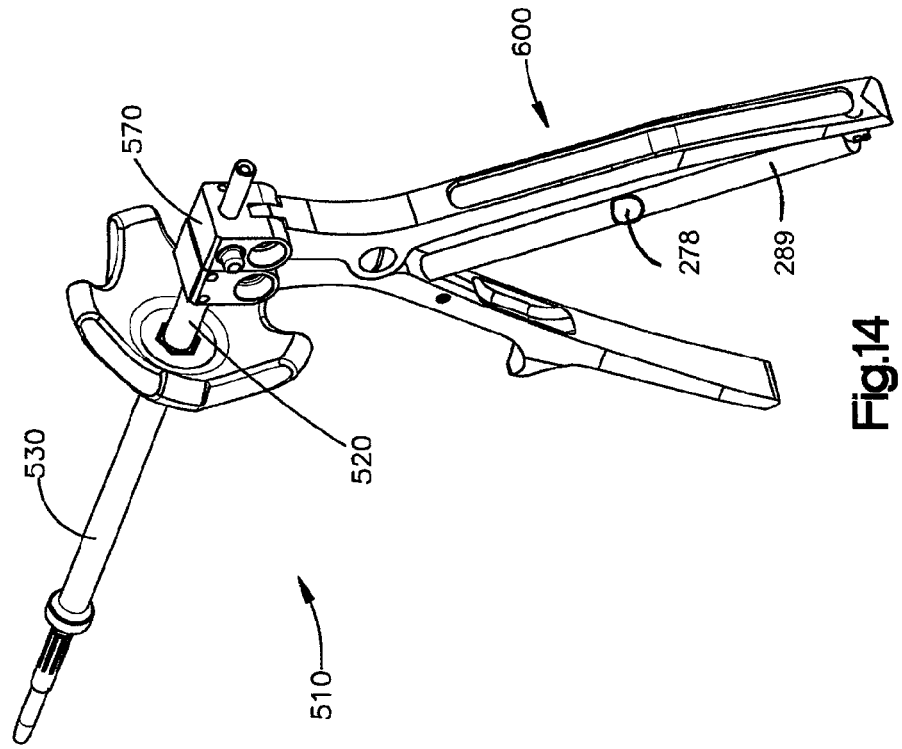
FIG. 14 is a perspective view of the surgical instrument constructed in accordance with another embodiment including a housing, a socket assembly, a manipulating assembly, a gripping assembly and a reduction assembly, showing the surgical instrument engaged with an extension member.

FIGS. 14 and 15 display alternate arrangements and alternate components for surgical instrument 10. Reference numbers have been incremented by hundreds to denote similar components (such as socket assembly 30 in FIG. 2 and socket assembly 530 in FIG. 14). Referring to FIG. 14, an alternate embodiment of the surgical instrument 510 includes a housing 520, a socket assembly 530, a manipulating assembly 550, a gripping assembly 570 and a reduction assembly 600. The embodiment in FIG. 14 is structured and engages with an extension member 400 similarly to what has been described above in regards to the to the embodiment of FIGS. 10 and 11. As illustrated, manipulating assembly 550 is attached to housing 520 distally of reduction assembly 600. This placement of manipulating assembly 550 makes this embodiment more compact than earlier described embodiments and may allow the surgeon more room to operate. Reduction assembly 600 can include the linear ratchet 289, described earlier in regards to FIG. 11, to hold the reduction after the surgeon releases the first and second gripping members 283, 284. The linear ratchet 289 includes a release 278 which can be used to disengage the ratchet mechanism and release the reduction.

Referring to FIG. 15, an alternate embodiment of the surgical instrument 710 includes a housing 720, a socket assembly 730, a manipulating assembly 750, a gripping assembly 770 and a reduction assembly 800. In the illustrated embodiment manipulating assembly 770 is mounted out of alignment with socket assembly 730. Alternatively, manipulating assembly 770 may be mounted perpendicularly to socket assembly 730. Manipulating assembly 770 includes gears 725 housed within manipulating assembly 770. Gears 725 are sized and arranged within housing 720 to provide for a change in direction of input to output torque (if needed) or a mechanical advantage. A torque member 60 (shown in FIG. 5) can be attached to manipulating assembly 770 to allow a surgeon to supply a torque to the extension member 400 to secure it to a bone anchor 7. Gripping assembly 770 includes a thumb screw 771 which is engaged with a flexible member 772. The flexible member 772 is attached to the reduction assembly 800 and includes an inner bore 773 that receives the extension member 300. When the thumb screw 771 is tightened, it bends flexible member 772 which causes the inner bore 773 to constrict. This constriction creates a pinching force with holds extension member 300 in place during the reduction of the clamp 9 onto the bone anchor 7 as described above.

It should be appreciated that a number of bone anchor extension members have been described herein. Thus a spinal fixation kit can be provided that includes a plurality of bone anchor extension members and a surgical instrument configured to engage with the plurality of bone anchor extension members.

It will be appreciated by those skilled in the art that changes could be made to the preferred embodiment described above without departing from the broad inventive concept thereof. It is understood, therefore, that this invention is not limited to the particular embodiment disclosed, but it is intended to cover modifications within the spirit and scope of the present invention as defined by the present description.

What is claimed:

1. A surgical instrument configured to fix a clamp to a bone fixation device, the surgical instrument comprising:
   a housing defining a proximal end and a distal and that is spaced from the proximal end along a longitudinal axis, the housing including a body member and a housing inner bore that extends through the body member along the longitudinal axis;
   a gripping assembly at least partially disposed in the housing inner bore, the gripping assembly configured to grip an extension member that is coupled to the bone fixation device;
   a drive member that is supported by the distal end of the housing, the drive member configured to receive the clamp, such that rotation of the drive member fixes the clamp to the bone fixation device once the drive member has received the clamp;
   a reduction assembly attached to the housing and moveably coupled to the gripping assembly, such that movement of the reduction assembly relative to the gripping assembly causes the gripping assembly to translate within the housing inner bore along the longitudinal axis relative to the drive member; and
   a manipulating assembly that is supported by the proximal end of the housing, the manipulating assembly rotationally coupled to the drive member, such that rotation of the manipulating assembly rotates the drive member.

2. The instrument of claim 1, wherein the drive member comprises a nut with multiple points.

3. The instrument of claim 1, wherein the manipulating assembly further comprises a torque member rotationally coupled to the drive member.

4. The instrument of claim 3, wherein the manipulating assembly comprises a coupling which allows for separation of the torque member with the manipulating assembly.

5. The instrument of claim 4, wherein the coupling comprises corresponding internal and external hex drives.

6. The instrument of claim 3, wherein the torque member comprises a T-handle.

7. The instrument of claim 1, wherein the gripping assembly comprises:
   a sleeve including an outer shell, a hollow interior, a tapered portion, and a threaded portion;
   a ball bearing assembly including a ball bearing housing and at least one ball bearing, the ball bearing housing comprising at least one recess to hold the at least one ball bearing, wherein the ball bearing assembly fits within and slidably engages the sleeve;
   a sleeve cap including a threaded section which releasably engages with the sleeve threaded portion;
   a first biasing member contained within the hollow interior of the sleeve between the ball bearing housing and the sleeve cap; and
   a rack member including an outer surface which slidably engages with the housing inner bore, a rack running longitudinally along the outer surface, and an internal bore, wherein the outer shell of the sleeve engages with the rack member internal bore.

8. The instrument of claim 7, wherein the first biasing member is a spring.

9. The instrument of claim 7, wherein the reduction assembly comprises:
   a frame attached to the housing;
   a handle; and
   a pinion coupled to the handle and positioned within the frame;
   wherein rotation of the handle causes rotation of the pinion which in turn causes translation of the rack member and the attached gripping assembly within the housing inner bore.

10. The instrument of claim 9, wherein the handle comprises a tab coupled to a bearing, and the bearing is coupled to the pinion such that rotation of the tab causes rotation of the bearing and the pinion.

11. The instrument of claim 10, wherein the tab is pivotally coupled to the bearing allowing the tab movement in an additional degree of freedom.

12. The instrument of claim 9, further comprising a catch attached to the frame comprising a stopper end, wherein the stopper end engages the pinion and while engaged prevents rotation of the pinion in one direction.

13. The instrument of claim 12, wherein the catch is pivotally attached to the frame and further comprises a release end, when the release end of the catch is pressed down the stopper end is disengaged from the pinion allowing the pinion to rotate in either direction.

14. The instrument of claim 13, further comprising a second biasing member contained within the housing inner bore and positioned between the gripping assembly and the manipulating assembly.

15. The instrument of claim 1, further comprising a stop contained within the housing inner bore, wherein a proximal end of the stop engages the manipulating assembly and a distal end of the stop is positioned to mechanically interfere with the gripping assembly to limit translation of the gripping assembly within the housing inner bore.

16. The instrument of claim 1, further comprising a socket assembly supported by the distal end of the housing, the socket assembly including a socket shaft that extends from the housing, wherein the drive member is supported by the socket shaft.

17. The instrument of claim 16, wherein the socket assembly includes a socket bore extending through the socket shaft along the longitudinal axis, the socket bore being configured to receive the extension member.

18. The instrument of claim 17, wherein the socket shaft comprises at least one recess which provides visibility into the socket bore and the received extension member.

19. The instrument of claim 18, wherein the socket shaft comprises depth indicators along the recess.

20. The instrument of claim 16, wherein the manipulating assembly is rotationally coupled to the socket assembly, such that rotation of the manipulating assembly rotates the drive member.

21. A surgical instrument for fixing a clamp to a bone fixation device, the instrument comprising:
   a housing including a body member with an inner bore extending through the body;
   an interference fitting movably attached to the housing;
   a drive member supported by the housing, the drive member configured to receive the clamp, such that rotation of the drive member fixes the clamp to the bone fixation device once the drive member has received the clamp;
   a reduction assembly attached to the housing and moveably coupled to the interference assembly such that movement of the reduction assembly causes the interference fitting to move relative to the drive member; and
   a torque member supported by the housing, the torque member rotationally coupled to the drive member such that rotation of the torque member rotates the drive member.

22. The instrument of claim 21, wherein the interference fitting comprises a body and a recess, wherein the recess contains a pass-through portion and a blocking portion.

23. The instrument of claim 22, wherein the pass-through portion is sized to allow an extension member to move through the interference fitting and the blocking portion is sized to prevent the extension member from passing through the interference fitting.

24. The instrument of claim 23, wherein the reduction assembly comprises:
   a first attachment member connected to the housing in a fixed position relative to the housing;
   a second attachment member slidably connected to the housing;
   a first gripping member comprising a first portion and a second portion, the first portion being connected to the first attachment member; and
   a second gripping member comprising a first portion and a second portion, the first portion being connected to the second attachment member;
   wherein the first gripping member is hingedly connected to the second gripping member.

25. The instrument of claim 24, wherein as the second portions of the first and second gripping members are biased closer, the first portions of the first and second gripping members are biased apart.

26. The instrument of claim 25, wherein the reduction assembly further comprises a torque limiter connected to the second portions of the first and second gripping members.

27. A kit comprising:
   a surgical instrument configured to fix a clamp to a bone fixation device, the surgical instrument comprising:
      a housing including a body member extending around a longitudinal axis and a bore extending through the body member along the longitudinal axis;
      a socket assembly including a socket shaft, a bore extending through the socket shaft, and a drive member which receives the clamp, wherein a proximal end of the socket shaft engages the housing and a distal end of the socket shaft contains the drive member;
      a manipulating assembly that defines a proximal end and a distal end, wherein the distal end of the manipulating assembly engages the housing;
      a gripping assembly disposed in the bore of the housing; and
      a reduction assembly attached to the housing and moveably coupled to the gripping assembly;
      wherein movement of the reduction assembly causes the gripping assembly to translate within the bore of the housing along the longitudinal axis; and
   a plurality of bone anchor extension members, each bone anchor extension member comprising:
      a shaft that includes:
         (i) a distal portion which is threaded and configured to engage corresponding threads of a bone fixation device, the distal portion including a stop to limit insertion depth of the bone anchor extension member into the bone fixation device;

(ii) an opposed proximal portion including an engagement assembly, the engagement assembly having an outer diameter smaller than the bore of the housing and configured to be engaged by the gripping assembly; and (iii) an intermediate portion connected between the distal portion and the proximal portion;

wherein the engagement assembly has a maximum outer diameter configured to pass through an inner bore of a spinal fixation clamp.

28. A kit comprising:

a surgical instrument for fixing a clamp to a bone fixation device, the instrument comprising:
   a housing including a body member with an inner bore;
   a socket assembly including a socket shaft, an inner bore and a drive feature,
wherein a proximal end of the socket shaft engages the housing and a distal end of the socket shaft contains the drive feature;
   a manipulating assembly including a torque member, wherein a proximal end of the manipulating assembly contains the torque member and the distal end of the manipulating assembly engages the housing;
   an interference fitting, the interference fitting moveably attached to the housing; and
   a reduction assembly attached to the housing and coupled to the interference fitting;
wherein movement of the reduction assembly causes the interference fitting to slide along the body member of the housing in a direction away from the socket assembly; and
a plurality of bone anchor extension members, each bone anchor extension member comprising:
   a shaft that includes:
      (i) a distal portion which is threaded and configured to engage corresponding threads of a bone fixation device, the distal portion including a stop to limit insertion depth of the bone anchor extension member into the bone fixation device;
      (ii) an opposed proximal portion including an engagement assembly, the engagement assembly comprising a plurality of tapered segments arranged in series wherein each of the tapered segments is narrower toward its proximal end and wider at its distal end and the tapered segments are configured to engage with an interference member in a surgical instrument; and
      (iii) an intermediate portion connected between the distal portion and the proximal portion;
      wherein the engagement assembly has a maximum outer diameter configured to pass through an inner bore of a spinal fixation clamp.

29. A surgical instrument configured to fix a clamp to a bone fixation device, the surgical instrument comprising:
   a housing including a body member extending elongate along a longitudinal axis, the housing defining a housing inner bore extending through the body member along the longitudinal axis;
   a socket assembly including a socket shaft, a socket bore extending through the socket shaft, and a drive member which receives the clamp, wherein a proximal end of the socket shaft engages the housing and a distal end of the socket shaft contains the drive member;
   a manipulating assembly that defines a proximal end and a distal end, wherein the distal end of the manipulating assembly engages the housing;
   a gripping assembly disposed in the housing inner bore, the gripping assembly having:
      a sleeve including an outer shell, a hollow interior, a tapered portion, and a threaded portion;
      a ball bearing assembly including a ball bearing housing and at least one ball bearing, the ball bearing housing comprising at least one recess to hold the at least one ball bearing, wherein the ball bearing assembly fits within and slidably engages the sleeve;
      a sleeve cap including a threaded section which releasably engages with the sleeve threaded portion;
      a first biasing member contained within the hollow interior of the sleeve between the ball bearing housing and the sleeve cap; and
      a rack member including an outer surface which slidably engages with the housing inner bore, a rack running longitudinally along the outer surface, and an internal bore, wherein the outer shell of the sleeve engages with the rack member internal bore; and
   a reduction assembly attached to the housing and moveably coupled to the gripping assembly;
wherein movement of the reduction assembly causes the gripping assembly to translate within the housing inner bore along the longitudinal axis.

30. The instrument of claim 29, wherein the first biasing member is a spring.

31. The instrument of claim 29, wherein the reduction assembly comprises:
   a frame attached to the housing;
   a handle; and
   a pinion coupled to the handle and positioned within the frame;
   wherein rotation of the handle causes rotation of the pinion which in turn causes translation of the rack member and the attached gripping assembly within the housing inner bore.

32. The instrument of claim 31, wherein the handle comprises a tab coupled to a bearing, and the bearing is coupled to the pinion such that rotation of the tab causes rotation of the bearing and the pinion.

33. The instrument of claim 32, wherein the tab is pivotally coupled to the bearing allowing the tab movement in an additional degree of freedom.

34. The instrument of claim 31, further comprising a catch attached to the frame comprising a stopper end, wherein the stopper end engages the pinion and while engaged prevents rotation of the pinion in one direction.

35. The instrument of claim 34, wherein the catch is pivotally attached to the frame and further comprises a release end, when the release end of the catch is pressed down the stopper end is disengaged from the pinion allowing the pinion to rotate in either direction.

36. The instrument of claim 35, further comprising a second biasing member contained within the housing inner bore and positioned between the gripping assembly and the distal end of the manipulating assembly.

37. A surgical instrument for fixing a clamp to a bone fixation device, the instrument comprising:
   a housing including a body member with an inner bore;
   a socket assembly including a socket shaft, an inner bore and a drive feature, wherein a proximal end of the socket shaft engages the housing and a distal end of the socket shaft contains the drive feature;
   a manipulating assembly including a torque member, wherein a proximal end of the manipulating assembly contains the torque member and a distal end of the manipulating assembly engages the housing;

an interference fitting moveably attached to the housing, the interference fitting including a body and a recess, the recess containing a pass-through portion and a blocking portion; and a reduction assembly attached to the housing and coupled to the interference fitting;

wherein movement of the reduction assembly causes the interference fitting to slide along the body member of the housing in a direction away from the socket assembly.

38. The instrument of claim 37, wherein the pass-through portion is sized to allow an extension member to move through the interference fitting and the blocking portion is sized to prevent the extension member from passing through the interference fitting.

39. The instrument of claim 38, wherein the reduction assembly comprises:

a first attachment member connected to the housing in a fixed position relative to the housing;

a second attachment member slidably connected to the housing proximal to the first attachment member;

a first gripping member comprising a first portion and a second portion, the first portion being connected to the first attachment member; and a second gripping member comprising a first portion and a second portion, the first portion being connected to the second attachment member;

wherein the first gripping member is hingedly connected to the second gripping member.

40. The instrument of claim 39, wherein as the second portions of the first and second gripping members are biased closer, the first portions of the first and second gripping members are biased apart.

41. The instrument of claim 40, wherein the reduction assembly further comprises a torque limiter connected to the second portions of the first and second gripping members.

* * * * *